(12) United States Patent
Kassatly et al.

(10) Patent No.: US 9,610,417 B2
(45) Date of Patent: Apr. 4, 2017

(54) PORTABLE DISCONTINUOUS POSITIVE AIRWAY PRESSURE (DPAP) DEVICE AND METHOD OF USING THE SAME

(71) Applicants: Gabrielle M Kassatly, San Jose, CA (US); Danielle M Kassatly, San Jose, CA (US); Michelle M Kassatly, San Jose, CA (US); L. Samuel A Kassatly, San Jose, CA (US)

(72) Inventors: Gabrielle M Kassatly, San Jose, CA (US); Danielle M Kassatly, San Jose, CA (US); Michelle M Kassatly, San Jose, CA (US); L. Samuel A Kassatly, San Jose, CA (US)

(*) Notice: Subject to any disclaimer, the term of this patent is extended or adjusted under 35 U.S.C. 154(b) by 714 days.

(21) Appl. No.: 13/889,316

(22) Filed: May 7, 2013

(65) Prior Publication Data

US 2014/0332010 A1 Nov. 13, 2014

(51) Int. Cl.
*A61M 16/00* (2006.01)
*A61M 16/06* (2006.01)
(Continued)

(52) U.S. Cl.
CPC .... *A61M 16/0069* (2014.02); *A61M 16/0051* (2013.01); *A61M 16/0493* (2014.02);
(Continued)

(58) Field of Classification Search
CPC .......... A61M 16/0069; A61M 16/0051; A61M 16/0493; A61M 16/20; A61M 2205/8256;
(Continued)

(56) References Cited

U.S. PATENT DOCUMENTS

| 3,730,179 A | 5/1973 | Williams |
| 4,655,213 A | 4/1987 | Rapoport et al. |

(Continued)

OTHER PUBLICATIONS

R. Pierce, et al., "Upper Airway Collapsibility, Dilator Muscle Activation and Resistance in Sleep Apnoea," European Respiratory Journal, vol. 30, No. 2, pp. 345-353 (2007).

(Continued)

*Primary Examiner* — Tan-Uyen (Jackie) T Ho
*Assistant Examiner* — Elliot S Ruddie
(74) *Attorney, Agent, or Firm* — Samuel A Kassatly

(57) ABSTRACT

A portable, rechargeable, discontinuous positive airway pressure (DPAP) device for use by an individual as a breathing assist device. The DPAP device comprises a sensor for tracking an exhalation phase of a respiration cycle of the individual relative to a stimulation period, $E_O$. A stimulation source responsive to a sensor determination that the exhalation phase has entered the stimulation period, $E_O$, to discontinuously deliver a stimulation, during the stimulation period, $E_O$. A controller regulates the delivery of the stimulation by the stimulation source. A rechargeable power cell for power the controller. The rechargeable power cell includes a Seebeck element that is placed in contact with the individual's body for thermoelectrically converting the individual's body heat into an electrical current that recharges the power cell.

14 Claims, 30 Drawing Sheets

(51) Int. Cl.
*H02J 7/00* (2006.01)
*A61M 16/04* (2006.01)
*A61M 16/20* (2006.01)
*H01M 10/46* (2006.01)
*H02J 7/35* (2006.01)
*H02J 7/34* (2006.01)

(52) U.S. Cl.
CPC ............ *A61M 16/20* (2013.01); *H01M 10/46* (2013.01); *H02J 7/35* (2013.01); *A61M 2016/0021* (2013.01); *A61M 2016/0027* (2013.01); *A61M 2205/8256* (2013.01); *H02J 7/34* (2013.01)

(58) Field of Classification Search
CPC ... A61M 2016/0021; A61M 2016/0027; H02J 7/35; H02J 7/34; H01M 10/46
USPC .... 128/847, 204.18, 204.21, 204.23, 200.24, 128/200.26, 207.13, 207.14, 207.18; 320/101; 600/529–543; 607/35
See application file for complete search history.

(56) References Cited

U.S. PATENT DOCUMENTS

| | | | |
|---|---|---|---|
| 5,238,006 A | | 8/1993 | Markowitz |
| 5,433,193 A | | 7/1995 | Sanders et al. |
| 5,578,077 A | * | 11/1996 | Kassatly ...................... 623/3.13 |
| 5,954,050 A | | 9/1999 | Christopher |
| 6,516,805 B1 | * | 2/2003 | Thornton ..................... 128/848 |
| 7,353,826 B2 | | 4/2008 | Sleeper et al. |
| 7,481,224 B2 | | 1/2009 | Nelson et al. |
| 7,487,777 B2 | | 2/2009 | Gunaratnam et al. |
| 7,487,778 B2 | | 2/2009 | Freitag et al. |
| D589,140 S | | 3/2009 | Guney et al. |
| 7,533,670 B1 | * | 5/2009 | Freitag .................. A61M 16/00 128/204.18 |
| 7,578,013 B2 | | 8/2009 | Aikman |
| 7,578,294 B2 | | 8/2009 | Pierro et al. |
| 7,581,542 B2 | | 9/2009 | Abramson |
| 8,092,404 B2 | | 1/2012 | Kelly et al. |
| 8,172,912 B2 | | 5/2012 | Marsh et al. |
| 8,187,367 B2 | | 5/2012 | Wang |
| 8,191,551 B2 | | 6/2012 | Skovgard |
| 8,215,302 B2 | | 7/2012 | Kassatly et al. |
| 2002/0023648 A1 | * | 2/2002 | Komesaroff ............. 128/205.25 |
| 2008/0246439 A1 | * | 10/2008 | Tsui et al. ..................... 320/137 |
| 2010/0170513 A1 | * | 7/2010 | Bowditch ............. A61M 16/00 128/204.21 |
| 2012/0103336 A1 | * | 5/2012 | Evers ........................ 128/204.21 |
| 2012/0234323 A1 | * | 9/2012 | Connor ............. A61M 16/0066 128/204.21 |
| 2014/0261425 A1 | * | 9/2014 | Connor .................... 128/204.23 |

OTHER PUBLICATIONS

Isono S., et al., "Anatomy of Pharynx in Patients with Obstructive Sleep Apnea and in Normal Subjects," J Appl. Physiol. 1997: 82:1319-1326.

Shellock F. G., et al., "Occlusion and Narrowing of the Pharyngeal Airway in Obstructive Sleep Apnea: Evaluation by Ultrafast Spoiled GRASS MR Imaging," Am J of Roentgenology 1992:158:1019-1024.

Katherine Bourzac, "Power-Scavenging Batteries_MIT Technology Review," Aug. 25, 2011, available online at: http://www.technologyreview.com/news/425232/power-scavenging-batteries/ 11/29/2012.

* cited by examiner

PORTABLE DISCONTINUOUS POSITIVE AIRWAY PRESSURE (DPAP) DEVICE AND METHOD OF USING THE SAME

FIELD OF THE INVENTION

The present invention relates in general to the field of sleep disorders, breathing assist devices, and respiratory gas delivery systems, and in particular to a portable device, system, and method for reducing sleep disordered breathing events, such as sleep apnea and snoring.

BACKGROUND OF THE INVENTION

Sleep apnea is a breathing disorder characterized by brief disruptions of breathing during sleep. When a person stops breathing during sleep due to sleep apnea, the balance of oxygen and carbon dioxide in the blood is upset. This imbalance stimulates the brain to restart the breathing process. The brain signals the person to wake up so that the muscles of the tongue and throat can increase the size of the airway, by allowing carbon dioxide to escape and oxygen to enter the airway. These waking episodes are necessary to restart breathing, disrupt sleep, and may cause daytime exhaustion.

There are two types of sleep apnea: central and obstructive. Obstructive Sleep Apnea (OSA) and Central Sleep Apnea (CSA). OSA is the most common type of sleep apnea. It is caused by a breathing obstruction, which stops the airflow in the nose and mouth. CSA is less common than OSA, and is manifested as a central nervous system disorder that occurs when the brain signal telling the body to breathe is delayed. CSA can be caused by disease or injury involving the brainstem, such as a stroke, a brain tumor, a viral brain infection, or a chronic respiratory disease.

While the causes of apnea are different in CSA and OSA, the symptoms and results are generally similar, namely a deprivation of oxygen and poor sleep. The treatments for CSA include medications that stimulate the need to breathe and administration of oxygen. As used herein, sleep apnea includes either CSA or OSA.

Normally, the muscles of the upper part of the throat keep the airway open to permit airflow into the lungs. When the muscles of the upper airway relax and sag, the relaxed tissues may vibrate as air flows past the tissues during breathing, resulting in snoring.

When a person has OSA, the throat collapses during sleep, blocking the airway and preventing air from getting to the lungs. Generally, the throat muscles keep the throat and airway open. The resulting effect of OSA could become serious.

Exemplary sleep apneas treatment devices are described in the following publications: U.S. Pat. Nos. 4,655,213; 5,176,618; 5,238,006; 5,466,193; 7,353,826; 7,481,224; 7,487,777; 7,578,013; 7,578,294; 7,581,542; and D589140. Although several treatment devices have been described, the most common devices are classified into three categories: CPAP; dental appliances, oral devices, and lower jaw adjustment devices; and surgery.

CPAP (Continuous Positive Airway Pressure) is widely recommended for moderate to severe obstructive sleep apnea. CPAP entails wearing a mask-like device (or nose pillows) during sleep, in order to provide continuous, positive, pressurized air to prevent the airway from collapsing. While CPAP has proven to be effective for numerous patients, many people find the apparatus uncomfortable and awkward to use, particularly due to air leaks at higher pressures. Some improvements to the CPAP technology include options such as: "bilevel PAP," which switches from higher to lower air pressure during the expiration; and "AutoPAP," which uses an internal regulator that adjusts pressure rather than remaining at one fixed setting. Nonetheless, CPAP, as its name indicates, still uses "continuous" positive pressure.

Dental appliances, oral devices, and lower jaw adjustment devices may be made of acrylic and fit inside the mouth. Two oral devices that are commonly used are the mandibular repositioning device and the tongue-retaining device. These oral devices open the airway by bringing the lower jaw or tongue forward during sleep. While oral devices are more convenient to use than CPAP, they are generally more effective for mild to moderate sleep apnea cases. A number of side effects may result from the use of the dental appliances, such as soreness, and damage to, or permanent change in position of the jaw, teeth, and mouth; saliva build-up; and nausea.

Surgery can increase the size of the patient's airway. The surgeon may remove tonsils, adenoids, or excess tissue at the back of the throat or inside the nose. The surgeon may reconstruct the jaw to enlarge the upper airway. Surgery may be an effective option for some patients; however, surgery carries the risks of surgical complications and infections.

While the foregoing treatment devices are useful for their intended purposes, there remains an unsatisfied need for a simple, cost-effective device, system, and method for reducing sleep disordered breathing events.

In addition to the foregoing sleep disorder related concerns, another problem arises for patients who use current respiratory devices, namely the portability of the CPAP machines. A representative portable CPAP machine is the Transcend CPAP, which is described at the following web site: http://www.mytranscend.com/patients/why-transcend/, as having the following dimensions: 6.1"×3.5"×2.8". Although this device is relatively small, an extended use of this product may require an external battery, which adds to the size and weight of the CPAP machine. In addition, some of the limitations to the miniaturization of the Transcend CPAP may be: the continuous operation of the pump, the power supply, the pump design, and the electronic circuitry.

Therefore, there still remains an unsatisfied need for a simple, cost-effective portable breathing aid device, system, and method for more efficiently and economically providing added comfort to the users.

SUMMARY OF THE INVENTION

The present invention satisfies this need, and presents a device, system, and method for reducing sleep disordered breathing events (collectively referred to herein as "DPAP device", "the present DPAP device", or "Discontinuous Positive Airway Pressure Device").

The present DPAP device provides selective excitation to the pharyngeal conduit or another muscle or cartilage along the respiratory path, a predetermined period of time before the end of the expiration stage, in order to prematurely reverse the respiratory cycle before the total collapse of the pharyngeal conduit, thus enabling the inhalation stage to reopen and refill the pharyngeal conduit.

According to other embodiments of the present invention, the excitation source includes a puff of positive air pressure, oxygen, another gas, electrical, and/or an audible (or sound) vibratory wave.

According to still other embodiments, the excitation source is applied to pharyngeal conduit, the tongue, the palate, the epiglottis, salivary glands, and/or other muscles or cartilages that can cause the premature reversal of the respiratory cycle.

According to yet another embodiment, the DPAP device is a relatively small, portable, user-wearable, rechargeable, and cost-effective breathing aid (or assist) device that efficiently and economically provides added comfort to the user. The DPAP device induces a premature inhalations cycle, as needed, to avoid having the brain signal the user to wake up so that the muscles of the tongue and throat can increase the size of the airway.

To this end, the DPAP device includes a sensor that identifies a breathing back pressure below a predetermined threshold, as the exhalation cycle approaches its virtual end.

The stimulation provided by the DPAP device can be either gradual (i.e., soft) or stepped (i.e., hard). When using the gradual stimulation, if after a predetermined time period the induced (or natural) inhalation cycle does not start, then the DPAP device has the following two alternative options:

The first option is for the DPAP device to continue the course of the gradual stimulation until it reaches a sufficient stimulation level.

The second option is for the DPAP device to apply a discrete stimulation that induces the premature inhalation.

According to a preferred embodiment, the DPAP device uses a dental appliance. The dental appliance may be made integrally with, and of the same material as the oral tube. The dental appliance includes a formable or compliant section that fits over the user's teeth or gum, and an internal extension. The dental appliance includes an opening that enables the stimulation to be nozzled out of an outlet opening, directionally toward an intended target stimulation area.

According to a specific embodiment, the DPAP device establishes a wireless (or remote) communication with an external communication device, such as a smart phone and/or an external processor.

During regular breathing events, the teeth slightly pressed against the pliable section and deform it slightly so that it forms a resting seat for the upper teeth. During regular breathing events, the pliable section of the resting seat does not restrict the flow of fluid within the oral tube. The dental appliance maintains the upper and lower teeth slightly separated.

The dental appliance includes a valve is normally closed as long as the user does not grind the upper and lower teeth. The grinding motion closes the pliable section of the resting seat, and a backpressure is built within the dental appliance. This back pressure causes the valve to open and to direct the stimulation toward the teeth. Once the grinding action stops, the flow through the nozzled opening resumes and the valve is closed.

According to another embodiment, the DPAP device is used with a nasal tube. The nasal tube is typically looped around the user's ears and delivers the stimulation to the nasal cavity. As the stimulation enters the nasal cavity, it expands and vaporizes into particles that stimulate the user's olfactory senses and cause a reaction of the uvula, thus clearing the airways for breathing.

According to another embodiment it would be possible to incite the desired breathing response of a user, by stimulating various parts of the user's body, for example, the user's ear, the top of the head, or the scalp. The stimulation can be done by means of one or a plurality of holes, openings, or nozzles disposed along the nasal tube in order to allow at least some of the stimulation to escape and stimulate the target area.

According to another embodiment, one such opening is positioned in close proximity to the user's ears to generate an auditory stimulation, such as a high frequency pitch that causes the desired respiratory response.

Another DPAP device according to an alternative embodiment of the present invention, can be used as a retrofit to an existing CPAP device. The DPAP device makes use of the pumping force of the conventional CPAP device. The DPAP device includes a respiration sensor that can be worn by the user like a necklace due to its miniaturized size, as explained earlier. The respiration sensor senses the onset of the exhalation stage and the approach of the stimulation point, E. To this end, the sensor is connected to the nasal tube and is also connected to a valve via a fluid tube. The valve controls the flow of air from the CPAP device so that the DPAP device operates similarly to the DPAP device. The valve is connected at its other end, to the hose. The valve can include a flow reducer that controls the rate of flow, the volume, and the pressure of the stimulation.

According to another design, the sensor is connected to the control circuitry of the CPAP device. Alternatively, the operation of the CPAP device can be reprogrammed to respond to the sensor and to operate the CPAP device according to the teachings of the present invention.

According to a specific embodiment, the DPAP device includes an infusion pump with one or more inlet port and one or more outlet port that permit the exchange of fluid. The inlet port and the outlet port are concentric. In one specific embodiment, the infusion pump is a dual-spiral infusion pump In the latter embodiment, the DPAP device includes a power cell that comprises a rechargeable battery charged by two or more charging devices, such as a Seebeck charger and a solar charger.

According to another embodiment, the DPAP device is used with a smart phone and/or an external processor. The DPAP device includes the power cell that supplies the necessary power to a stimulation source, a respiration sensor, and a transceiver. The power cell further includes an additional charging element, namely a piezoelectric vibration element that converts the vibrations of the DPAP device into electrical current that further charges the rechargeable battery. The vibration frequency of the piezoelectric vibration element can be set to a predetermined resonance frequency that maximizes the resonance, and thus maximizes the energy conversion from vibration to electrical.

The power cell of the DPAP device may further include a heat absorbent surface or heat sink that absorbs externally generated heat.

The power cell of the DPAP device may further be provided with an inductive element that inductively interacts with a similarly and generally oppositely situated inductive element, to provide vibration to the piezoelectric vibration element, to heat the Seebeck charger, and wherein excess heat is absorbed by the heat absorbent surface, thus minimizing energy loss.

The DPAP device may be provided with a dual-spiral infusion pump. Alternatively, the DPAP device may be provided with an expansion dual-spiral pump.

According to another embodiment, the DPAP device may be provided with a dual function infusion/expansion pump. In operation, during the inhalation stage, the pump intakes air and compresses it for exhaust through the nasal tube.

During the expiration stage, the exhaled carbon dioxide is pulled into the pump and expanded for exhaust.

According to still another embodiment, the DPAP device uses a pressurized cartridge as a stimulation source.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

FIGS. 3 and 4 are flow charts illustrating the process of using the DPAP device of FIG. 1 for reducing sleep disordered breathing events, as shown in the chart of FIG. 2, wherein FIG. 3 illustrates the general steps of a method for initializing the DPAP device of FIGS. 1 and 2, and further wherein FIG. 4 illustrates the general steps of a method using the DPAP device of FIGS. 1 and 2;

It should be understood that the sizes of the chart and the different components in the figures might not be in exact proportion, and are shown for visual clarity and for the purpose of explanation.

DETAILED DESCRIPTION OF PREFERRED EMBODIMENTS

Reference is made herein to two related U.S. Pat. Nos. 5,578,077 and 8,215,302, both of which are incorporated herein by this reference, in their entirety.

Figure 1:
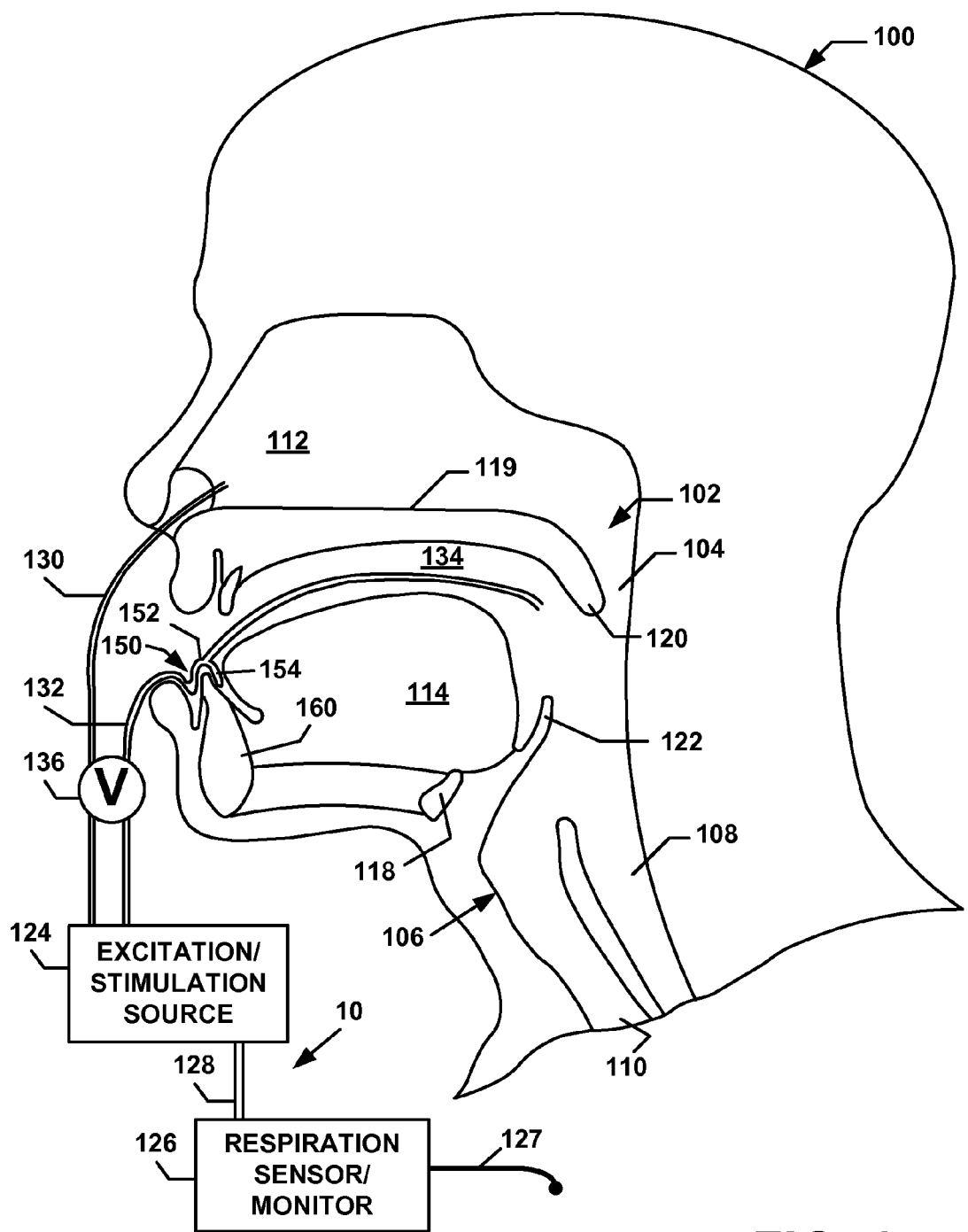
FIG. 1 is a side, cross-sectional, elevational view of a person's head showing a DPAP device according to the present invention.

FIG. 1 is a side view of a person's head 100 showing the placement of a DPAP device 10 according to the present invention. The person's upper airway 102 includes the pharynx 104 that splits into the larynx/trachea 106 and the esophagus 108. Although the tissue along this airway is responsive to the respiratory cycle, only the pharyngeal conduit 110, that includes the tissues in the region of the upper airway 102 that starts behind the nasal cavity 112 and ends in its connections to the larynx 106, is totally collapsible.

The pharyngeal structure and individual anatomic components within the upper airway 102 include the pharyngeal walls; the base of the tongue 114; the vallecula (or epiglottic vallecula); the hyoid bone 118 and its attachments; the soft palate 119 with uvula 120, the palatine tonsils with associated pillar tissue; and the epiglottis 122.

Figure 2:
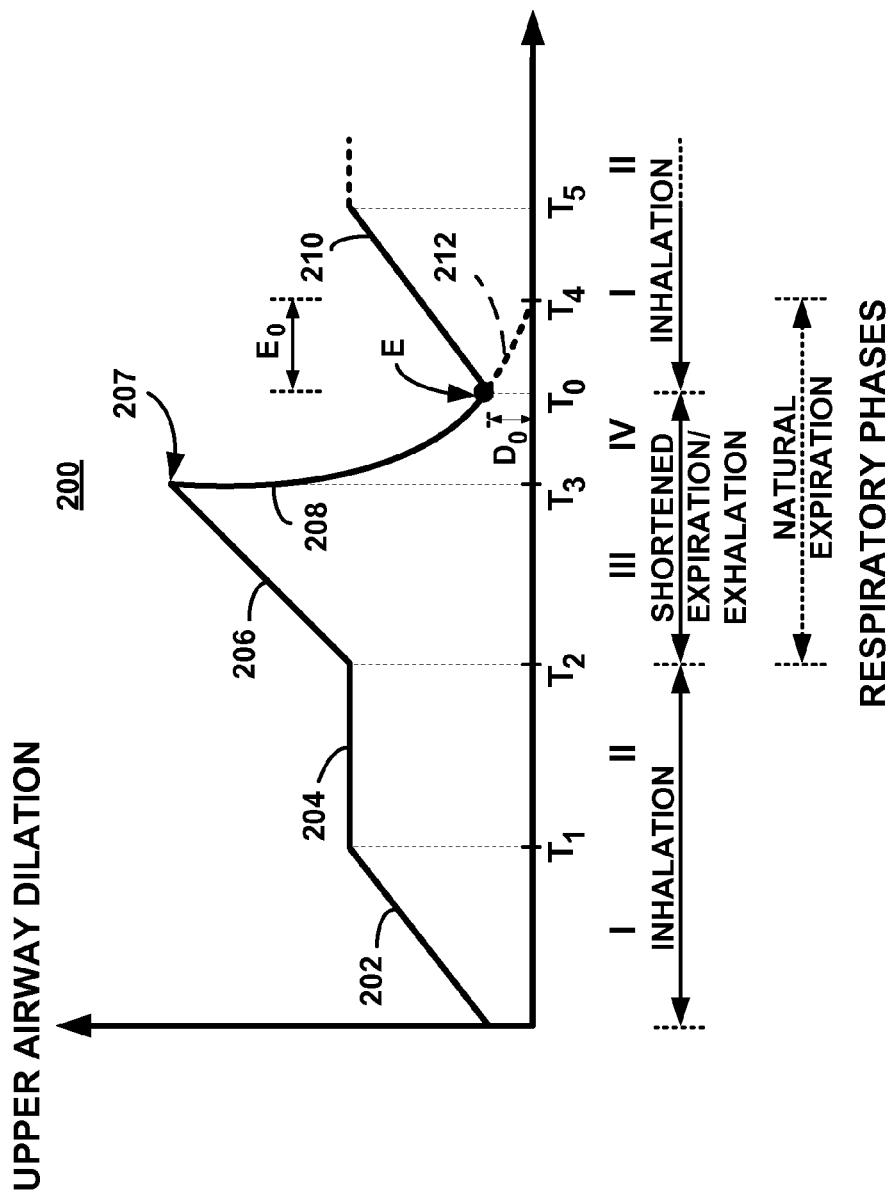
FIG. 2 is a graph illustrating the respiratory cycle using the DPAP device of FIG. 1.

FIG. 2 is a chart that illustrates an exemplary respiratory cycle 200 using the DPAP device 10 of FIG. 1 according to the present invention. This chart illustrates the variation (or dilation) of the cross-sectional area of the upper airway 102, with respect to the various phases of the respiratory cycle 200. At the initiation of inspiration (Phase I), and as illustrated by the segment 202, which ends at $T_1$, the upper airway 102 begins to dilate. Thereafter, and as illustrated by the segment 204, that ends at $T_2$, the upper airway 102 remains relatively constant through the remainder of inspiration (Phase II).

At the onset of expiration (Phase III), and as illustrated by the segment 206, that ends at $T_3$, the upper airway 102 begins to enlarge or dilate, reaching a maximum diameter at point 207. The upper airway 102 then starts to diminish in size, as illustrated by the segment 208, so that at the end of the natural expiration, without the corrective excitation of the present invention), it is at its narrowest, corresponding to the time $T_4$ when the upper airway (102) dilator muscles are least active, and positive intraluminal pressure is lowest.

The pharyngeal conduit 110 has the greatest potential for collapse and closure at the end of the expiration stage (at time $T_4$). The dilator muscle activation is directly related to airway narrowing and reduces resistance across patients with obstructive sleep apnea. R. Pierce, et al., "Upper Airway Collapsibility, Dilator Muscle Activation And Resistance In Sleep Apnoea," European Respiratory Journal, Volume 30, Number 2, pages 345-353 (2007).

Sleep is characterized by a reduction in upper airway dilator muscle activity. For the person with obstructive sleep apnea (OSA), it is believed that this change in muscle function causes pharyngeal narrowing and collapse. Current studies seem to support that OSA patients have an intrinsically structurally narrowed and more collapsible pharynx. Isono S., et al., "Anatomy of Pharynx in Patients with Obstructive Sleep Apnea and in Normal Subjects," J. Appl. Physiol. 1997: 82:1319-1326.

Although anatomic closure is often accentuated at specific sites, such as the velopharyngeal level, studies of closing pressures show that the narrowing and collapse usually occurs along the entire length of the pharynx 104. Shellock F. G., et al., "Occlusion and Narrowing of the Pharyngeal Airway in Obstructive Sleep Apnea: Evaluation by Ultrafast Spoiled GRASS MR Imaging," Am J of Roentgenology 1992:158:1019-1024.

The DPAP device 10 reduces sleep disordered breathing events by selectively providing excitation to the pharyngeal conduit 110 or another muscle, cartilage, or element along the respiratory path of the upper airway 102 (collectively referred to herein as "selective elements of the pharyngeal conduit"). This excitation is introduced at an optimal excitation point, E, at time $T_0$, which is selected at a predetermined, but short, excitation period of time (or stimulation zone) $E_0$, before the virtual end, $T_4$, of the natural expiration stage. $T_0$-$T_4$ [$T_4$] is also referred to herein as "the virtual period".

The application of the excitation can also be quantified as a measure of the dilation of the pharyngeal conduit 110. In a preferred embodiment, the excitation (or stimulation) is applied as the dilation of the pharyngeal conduit 110 reaches approximately $D_0$. As a result, the excitation point E could be determined as a function of two parameters, the dilation $D_0$ and the excitation period $E_0$: $E(D_0, E_0)$.

These two parameters ($D_0$, $E_0$) vary for each individual, and are thus personalized. The selection of the excitation point E enables the premature reversal of the respiratory cycle before the total collapse of the pharyngeal conduit 110, and shortens the natural occurrence of the expiration or exhalation stage. As a result of such reversal, the inhalation stage is prematurely introduced, at about substantially the optimal excitation period $E_0$ prior to its natural initiation. The premature initiation of the inhalation phase (Phase I) prematurely reopens and commences the inflation of the pharyngeal conduit 110, prior to the expected total or substantial collapse of the pharyngeal conduit 110. The premature inflation of the pharyngeal conduit 110 prevents the occurrence of the apneic events.

More specifically, and still with reference to FIG. 2, the expiration stage is cut off at time $T_0$. Rather than allowing the pharyngeal conduit 110 to follow its natural course and dilate, or more accurately deflate, following the path 212 (shown in dotted lines), the pharyngeal conduit 110 is forced to be inflated along the path 210 (that ends at $T_5$). Consequently, according to the present invention, the expiration stage (phases III and IV) is shortened relative to the natural, uncorrected, expiration cycle, in order to provide the corrective treatment.

If the pharyngeal conduit 110 were allowed to collapse totally or substantially, then it would require air at higher pressure to cause it to open. However, if the pharyngeal conduit 110 were allowed to partially collapse, the pressure required to open it and to inflate it would be significantly less than that required under the total collapse. As a result, the timing of the excitation according to the present invention is important to reduce the magnitude or amplitude of the excitation.

To this end, the DPAP device 10 includes an excitation (or stimulation) source 124 that is connected to a respiration sensor (or monitor) 126 via cables or fluid conduits 128 (that conduct a fluid or a gas). The respiration sensor 126 is provided with electrodes 127 that collect the desired respiration parameters, in order to allow the practitioner to personalize the optimal excitation point E for each individual.

One (or two) nasal tube (mask or wire) 130 is connected to the excitation source 124 at one end, with its other end partly inserted in (or covering) the nasal cavity 112. According to another preferred embodiment, an oral tube or an electrical wire 132, or a dental appliance 150, is connected to the excitation source 124 at one end, with its other end partly inserted in (or covering) the mouth 134. According to still another embodiment, both the nasal tube 130 and oral tube 132 are connected to the excitation source 124, by means of a valve 136.

Considering now the respiration sensor/monitor 126, its main functions are: (1) upon initialization of the DPAP device 10 for the first time, the respiration sensor/monitor 126 assists the practitioner to determine the optimal excitation point E for the particular use of the DPAP device 10; and (2) for the normal use of the device, the respiration sensor/monitor 126 confirms the occurrence or presence of the excitation point E, and upon such confirmation it provides the necessary excitation to the user of the DPAP device 10.

The respiration sensor/monitor 126 uses the electrodes 127 to monitor the respiratory cycle 200, and the progress of its four phases (I, II, III, IV), as is known or available in the field. As an example, the respiration sensor/monitor 126 monitors the variations in the relative position of the chest (as is currently done in a sleep study) in order to calculate the occurrence of the parameters of the excitation point E: the dilation $D_0$ and the excitation period $E_0$: $E(D_0, E_0)$.

According to another embodiment of the present invention, the respiration sensor/monitor 126 provides a feedback as to the efficacy of the excitation provided by the DPAP device 10 so as to vary the dilation $D_0$ and the excitation period $E_0$: $E(D_0, E_0)$ of the excitation point E.

As an example, under certain conditions, such as when the individual or user is sick and his/her respiration cycle does not follow the normal respiratory cycle. As an illustration, if the respiration sensor/monitor 126 determines the virtual time $T_4$, when the upper airway (102) dilator muscles are expected to be least active, and the positive intraluminal pressure is the lowest (from previous measurements during respiratory cycles), and further determines that this virtual time $T_4$ is different from the usual or normal virtual time $T_4$ that was determined at the initialization stage, then the respiration sensor/monitor 126 could automatically adjust the dilation parameter $D_0$ of the pharyngeal conduit 110 accordingly.

As another illustration, the respiration sensor/monitor 126 determines variations from the norm of the dilation parameter $D_0$ of the pharyngeal conduit 110, then it could automatically adjust the virtual time $T_4$, could accordingly. In a preferred embodiment, the dilation $D_0$ exceeds approximately 1 mm and the excitation period $E_0$ exceeds approximately 1 millisecond.

Considering now the excitation source 124 could provide a variety of excitations, some of which are: a puff of positive air pressure, oxygen, another gas, electrical, and/or an audible (or sound) vibratory wave. To this end, in order for the excitation source 124 to provide a short puff of air or gas (i.e., oxygen or another gas), the excitation source 124 includes a pump similar to that used in the CPAP device.

One distinction between the common CPAP device and the DPAP device 10 of the present invention is that in the present DPAP device 10 the puff of positive air is discontinuous, that is a puff of air is delivered at the desired pressure but only for a very short period of time, such as 0.5 second. Another desirable feature of the present DPAP device 10 is that the air puff pressure that this delivered intermittently (or periodically) could be lower than the pressure at which air is continuously delivered by the CPAP device, in that the air puff is delivered at the optimal excitation point E, prior to the collapse of the pharyngeal conduit 110.

According to another embodiment, in order for the excitation source 124 to provide an electrical excitation, the excitation source 124 includes an electrical stimulation device, such as those used, for example, in cardiac pacemakers or tachycardia devices.

According to still another embodiment, in order for the excitation source 124 to provide an audible (or sound) vibratory wave, the excitation source 124 includes a sound pressure pump capable of generating vibratory waves, such as sound waves or other audible waves that are not limited to the audible frequency spectrum. The vibratory frequencies of the waves are selected to selectively cause selected elements, muscles, ligaments, cartilage, or cavities to vibrate or resonate.

For example, the excitation source delivers a wave at, or about, the resonance or vibration frequency of the nasal cavity 112, at the excitation point E. According to still other embodiments, the excitation source 124 delivers a wave at, or about, the resonance or vibration of the pharyngeal conduit 110, the tongue 114, the palate 119, the epiglottis, the uvula 120, the salivary glands, the larynx/trachea 106, the esophagus 108, and/or other muscles or cartilages, including the hyoid bone 118, that can cause the premature reversal of the respiratory cycle 200, as described earlier.

In a specific preferred embodiment where the dental appliance 150 is used in conjunction with the oral tube 132 for delivering the puff of gas, the dental appliance 150 may be made of the same material as the oral tube 132 for allowing the gas to pass therethrough. It includes a formable or compliant section 152 that fits over the user's teeth or gum 160, and an internal extension 154. An oral extension extends from, and is in fluidic communication with the oral tube 132 via the compliant section 152, into the user's mouth 134.

Figure 3:
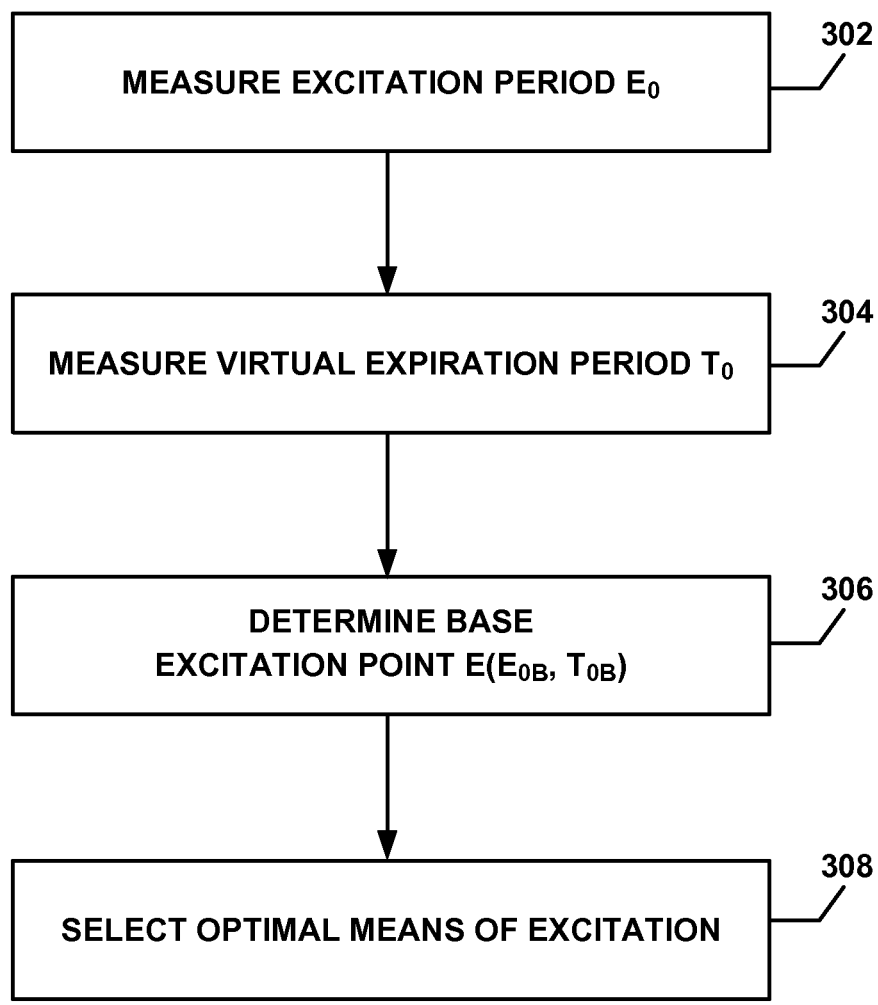
Figure 4:
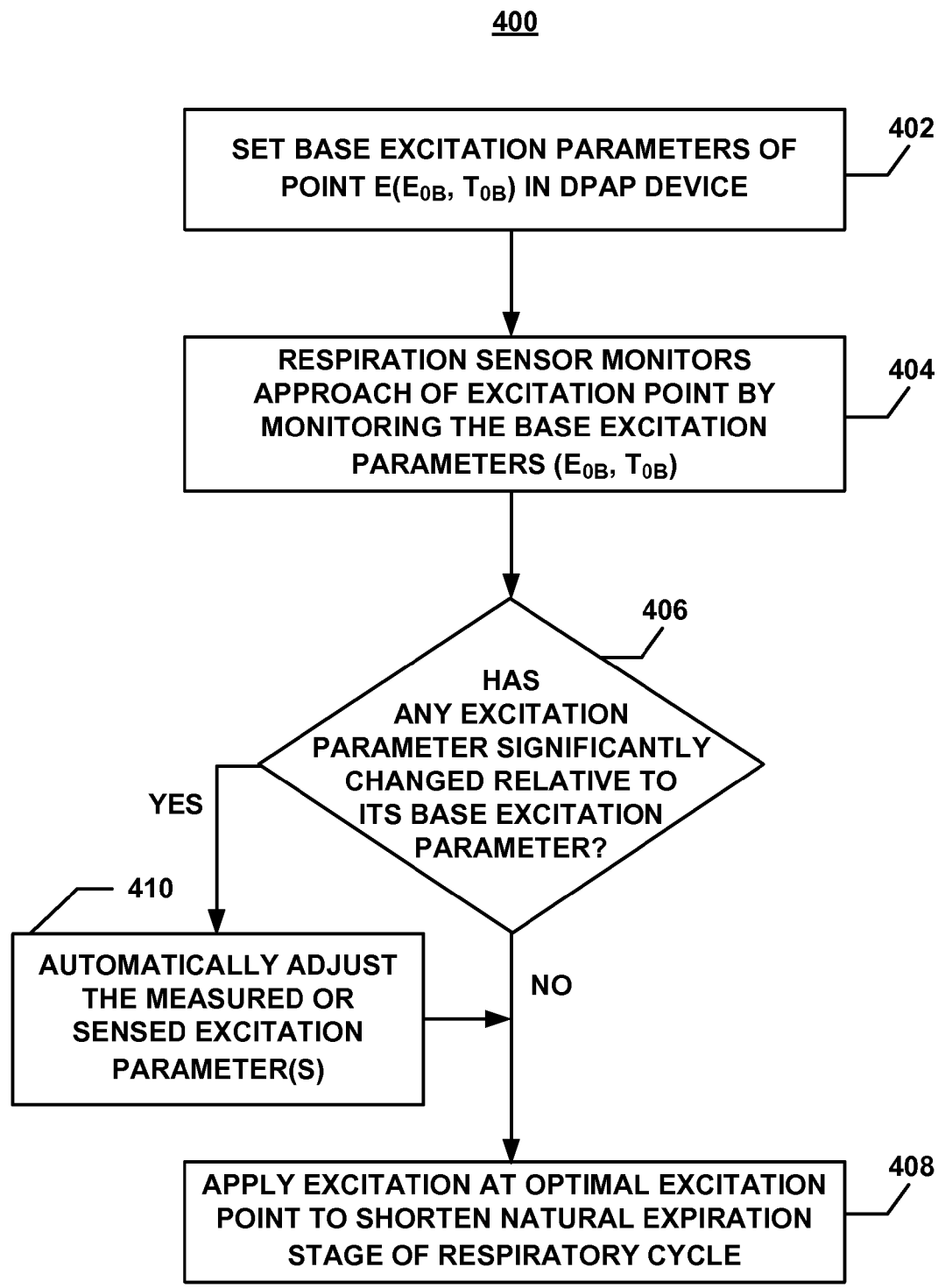

FIGS. 3 and 4 are flow charts illustrating the process of using the DPAP device 10 of FIG. 1 for reducing sleep disordered breathing events, as shown in the chart of FIG. 2. More specifically, FIG. 3 illustrates a method 300 for initializing the DPAP device of FIGS. 1 and 2.

At step 302, method 300 measures the base excitation period $E_{OB}$, pursuant to the chart of the respiratory cycle 200 of FIG. 2. At step 304, method 300 measures the base virtual period $T_{4B}$. Based on these parameters of the base excitation period $E_{OB}$ and the base virtual period $T_{4B}$, method 300 determines the optimal excitation point E for the particular user.

Considering now FIG. 4, it illustrates the general steps of a method 400 using the DPAP device 10 of FIG. 1 that has been initialized according to method 300 of the present invention. At step 402, method 400 sets the base excitation parameters ($E_{OB}$, $T_{4B}$) of the excitation point E that were determined pursuant to method 300 of FIG. 3.

At step 404, the respiration sensor 126 (FIG. 1) monitors the approach of the excitation parameters ($E_0$, $T_4$) of the excitation point E to their respective base values ($E_{OB}$, $T_{4B}$). At step 406, as soon as the excitation parameters reach, or closely approach, their respective base values ($E_{OB}$, $T_{4B}$), method 400 inquires if any of the excitation parameters ($E_0$, $T_4$) of the excitation point E has significantly changed relative to its respective base value ($E_{OB}$, $T_{4B}$), i.e., within an acceptable range, for instance 1% to 15%.

If method 400 determines that any of the excitation parameters ($E_0$, $T_4$) of the excitation point E has not significantly changed relative to its respective base values ($E_{OB}$, $T_{4B}$), then method 400 proceeds to step 408. At step 408, method 400 applies the excitation at the excitation point E, in order to shorten the natural excitation stage.

If method 400 determines at step 406 that one or both of the excitation parameters ($E_0$, $T_4$) of the excitation point E has significantly changed relative to its respective base values ($E_{OB}$, $T_{4B}$), then method 400 proceeds to step 410. At step 410, method 400 automatically adjusts the unchanged parameter and thus adjusts the occurrence of the excitation point E. Method 400 then proceeds to step 408 and applies the excitation at the excitation point E, in order to shorten the natural excitation stage.

It is to be understood that the specific embodiments of the invention that have been described are merely illustrative of certain application of the principle of the present invention. Numerous modifications may be made to the description herein, without departing from the spirit and scope of the present invention. More specifically, while the present embodiments of the invention refer to an exemplary medical oxygen cylinder, it should be clear that the present respiratory gas delivery device may be used in conjunction (or be integrated) with other systems, such as: chemical oxygen generators, emergency oxygen systems provided for example, on submarines and airplanes, self contained breathing apparatus (SCBA), diving breathing systems, breathing masks for firefighters, breathing masks during surgery, and in every situation or system that could benefit for the discontinuous gas delivery system described herein.

Figure 5:
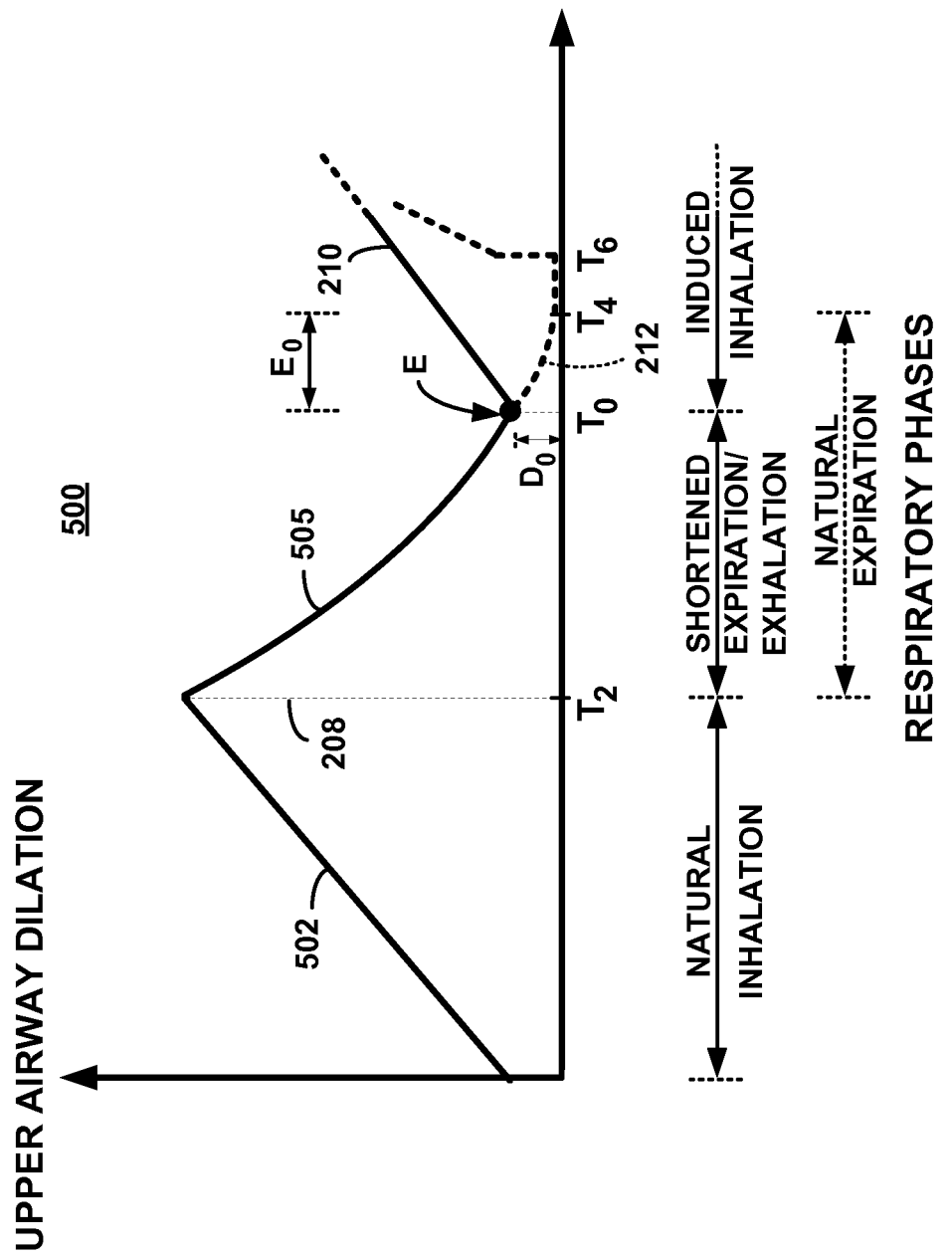
FIG. 5 is a graph that illustrates a simplified respiratory cycle, similar to that shown in FIG. 2, showing an exemplary virtual behavior, at $T_6$, when the brain signals the person who does not use the DPAP device, to wake up so that the muscles of the tongue and throat can increase the size of the airway.

FIG. 5 is a graph 500 that illustrates a simplified respiratory cycle, similar to that shown in FIG. 2, where the inhalation graph portion 502 replaces the graph sections 202, 204, and 206 (FIG. 2). Graph 500 illustrates an exemplary behavior, at time $T_6$, following the end of the expiration stage (at time $T_4$). At time $T_6$, the brain interprets the relatively flat line (shown in dotted line) of the graph 500, between $T_4$ and $T_6$, as the patient's inability to breathe, and signals the patient to wake up, so that the muscles of the tongue and throat can increase the size of the airway. The use of the DPAP device described herein introduces the stimulation, prior to time $T_4$ in order to induce a premature inhalation, thereby avoiding the brain induced event at $T_6$.

As stated earlier, the application of the excitation can be quantified as a measure of the dilation of the pharyngeal conduit 110. According to another embodiment of the present invention, the stimulation is applied when and if the sensor 126 identifies a breathing back pressure below a predetermined threshold, as the exhalation cycle approaches its virtual end at $T_4$.

According to still another embodiment of the present invention, the sensor 126 measures the rate of change of the exhalation graph, i.e., the derivative relative to time or instantaneous slope, of the exhalation graph portion 505. If, at any time, during the stimulation period $E_0$ the absolute value of the rate of change of the exhalation graph portion 505 is greater than a predetermined value for this particular patient, then a premature stimulation is introduced at E, in order to induce a premature inhalation. As a result, stimulation is delivery upon need, when necessary, in an attempt to anticipate and to prevent an apnea event.

Figure 6:
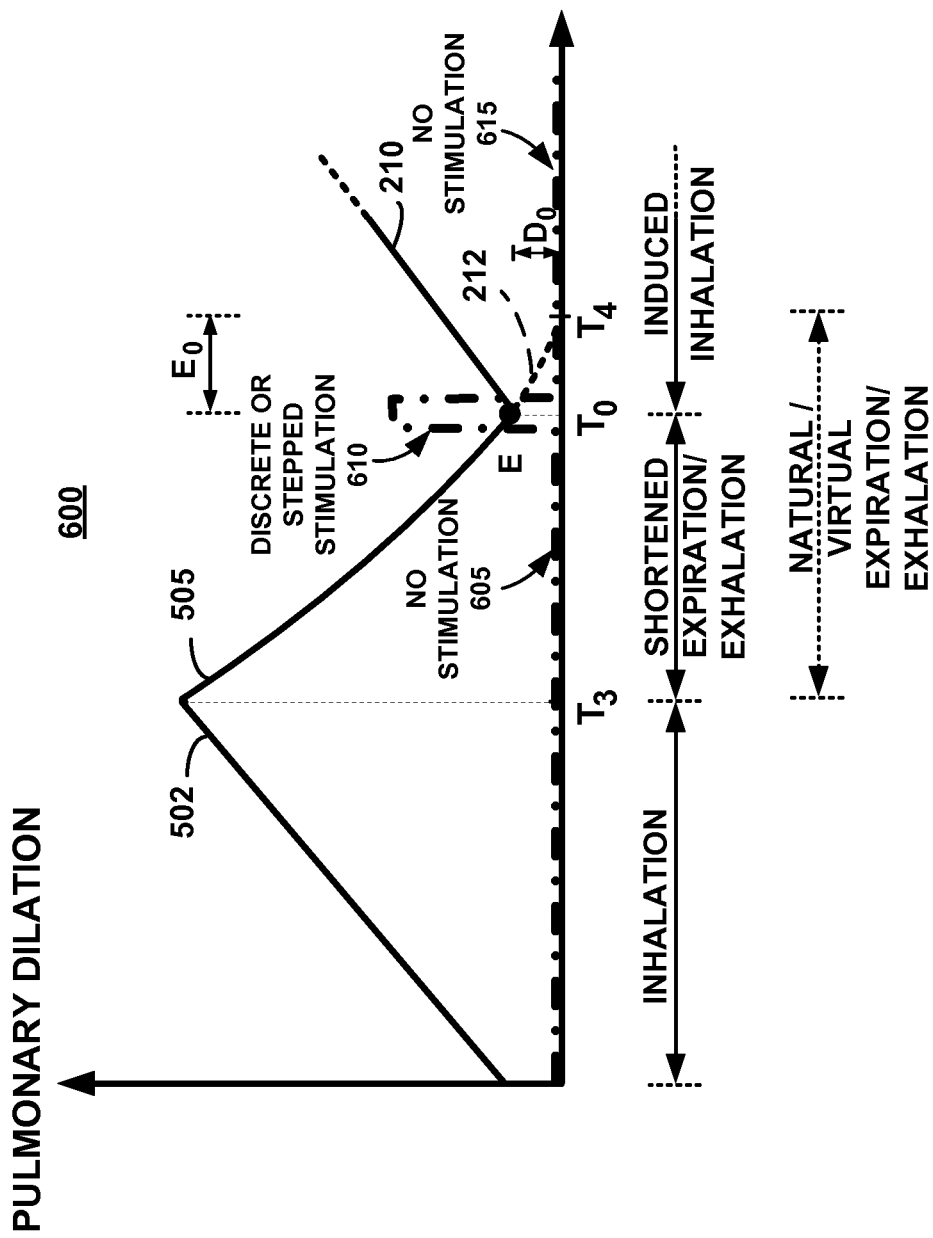
FIG. 6 is another graph that illustrates a simplified respiratory cycle, similar to that of FIG. 5, showing a discrete or stepped stimulation at the excitation point, E.

FIG. 6 is another graph 600 that illustrates a simplified respiratory cycle, similar to that of FIG. 5, showing the stimulation at the excitation point, E, or within the stimulation zone, $E_0$, as a discrete or stepped stimulation 610 that is preceded and succeeded by a lack of stimulation 605, 615, respectively, in order to induce a premature inhalation.

Figure 7A:
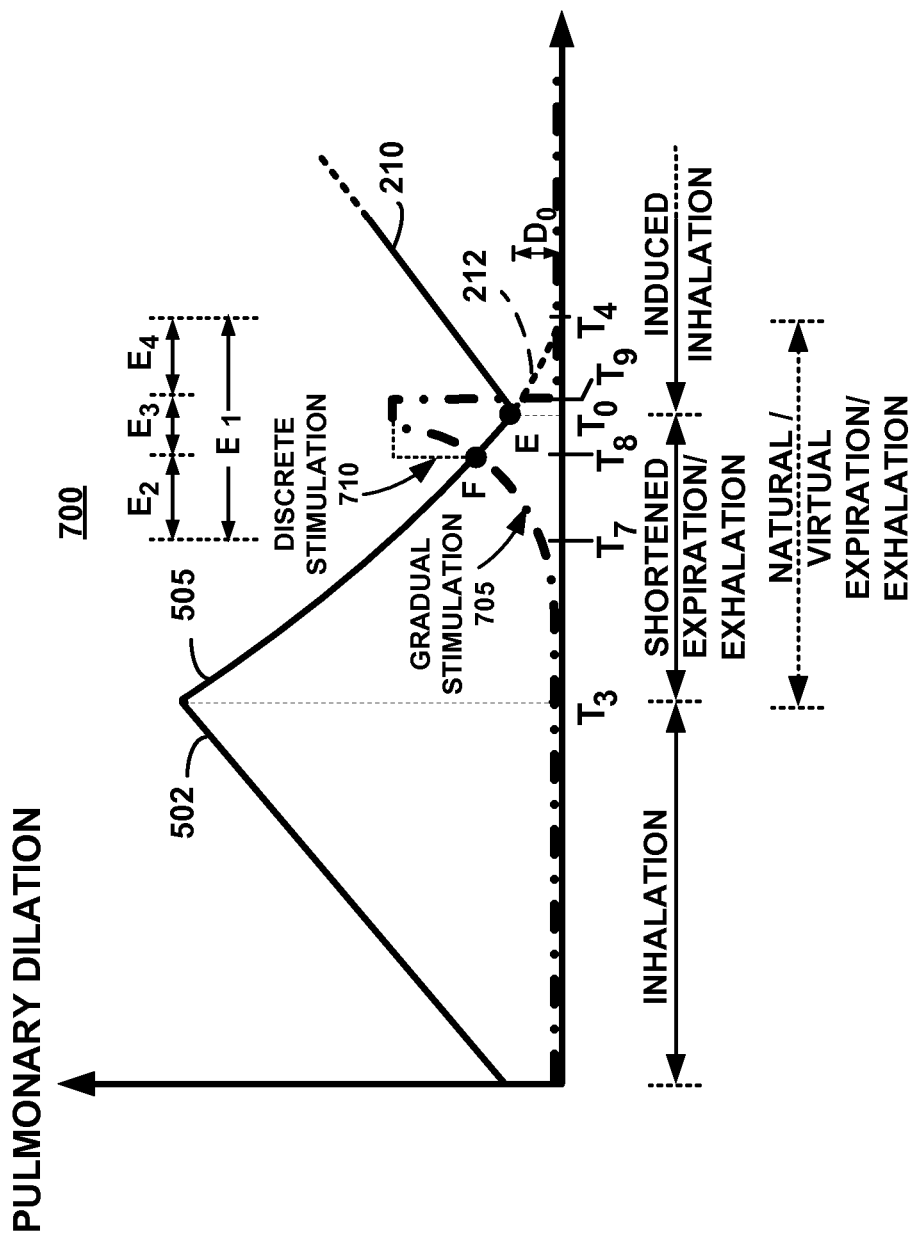
FIG. 7 is comprised of FIGS. 7A, 7B, and 7C, and illustrates three graphs of a simplified respiratory cycle, similar to that of FIG. 5, showing a gradual stimulation during the shortened expiration stage.

With reference to FIG. 7, FIG. 7A represents a graph 700 that illustrates a simplified respiratory cycle, similar to that of FIG. 5, showing a gradual (or soft) stimulation 705 during an extended stimulation period, $E_1$. The stimulation period, $E_1$, extends beyond the stimulation period $E_0$, so that the gradual stimulation 705 starts prematurely, at around time $T_7$, as shown, rather than around time $T_0$.

If after approximately a time period $E_2$, for example, at time $T_8$, either the natural or the induced inhalation cycle does not start (or is not induced), then the DPAP of the present invention has the following two alternative options:

The first option is for the DPAP to continue, at time $T_8$, the course of the gradual stimulation 705 until it reaches a sufficient stimulation level at time $T_0$ that corresponds to point E.

The second option is for the DPAP to apply, at a point F, that corresponds to time $T_8$, a discrete (or hard) stimulation 710 (shown in dotted line) that induces the premature inhalation 210 at approximately point E and that terminates at time $T_9$.

It should be noted that time $T_8$ may, but not necessarily, correspond to point F on the exhalation graph portion 505. In other terms, the gradual stimulation 705 in combination with the natural exhalation, are expected to induce a predetermined pulmonary (or pharyngeal) dilation at time $T_8$. If the latter dilation is not naturally attained at time $T_8$, then the stimulation is applied. Otherwise, neither the gradual stimulation 705 nor the discrete stimulation 710 is applied.

The advantage of this embodiment is that it minimizes the unnecessary application of stimulations, such as when the gradual stimulation 705 in combination with the patient's natural expiration induce an inhalation, prior to a safety time zone $E_4$. The safety time zone $E_4$ is defined as the difference between the extended stimulation period, $E_1$, and the sum of periods E1 and E2, as set forth in the following equation:

$$E_4 = E_1 - (E_2 + E_3),$$

Where $E_3$ represents the time period allocated to the application to either the gradual stimulation 705 or the discrete stimulation 710.

According to still another embodiment of the present invention, the soft stimulation or the hard stimulation following time $T_8$ are of different types. As an exemplary illustration only, the soft stimulation 705 prior to point F may be air, but the soft or hard stimulation following point F may be pure oxygen (or a different type of stimulation).

Figure 7B:
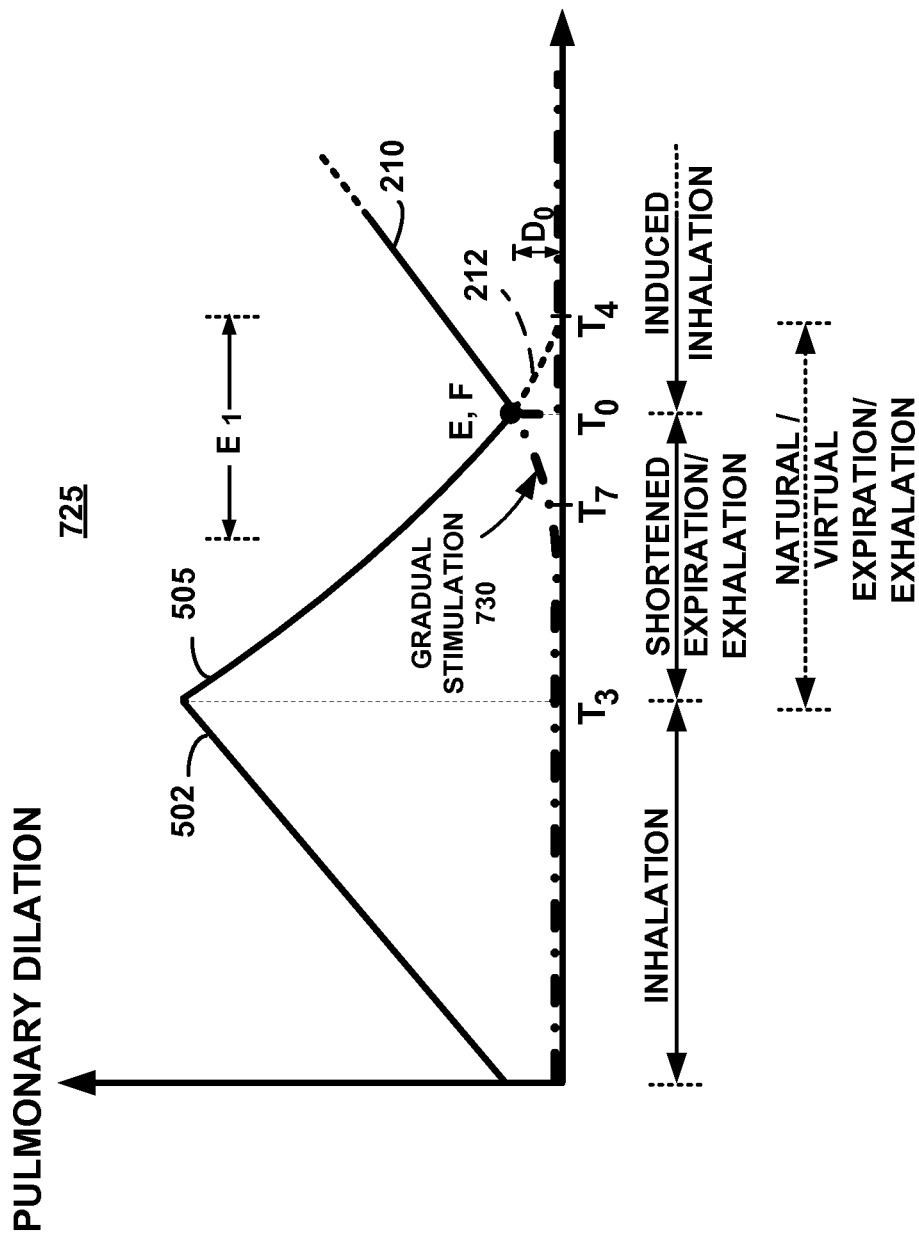

FIG. 7B illustrates another graph 725, wherein point F coincides approximately with point E, and the gradual stimulation 730 induces a premature inhalation, or the patient's natural inhalation is initiated on its own, then the stimulation 730 will no longer be allowed to unnecessarily increase, and will thus be interrupted.

This embodiment addresses the fact that current CPAP devices unnecessarily, continuously force air, and thus require continuous power even if the patient's own inhalation cycle starts naturally. As a result of the present reduction of power consumption during the inhalation stage and further during most of the exhalation stage, the power requirement to operate the present DPAP is significantly reduced, thus reducing the pump and battery sizes, rendering the DPAP amenable to being miniaturized, as it will be shown and explained herein.

Figure 7C:
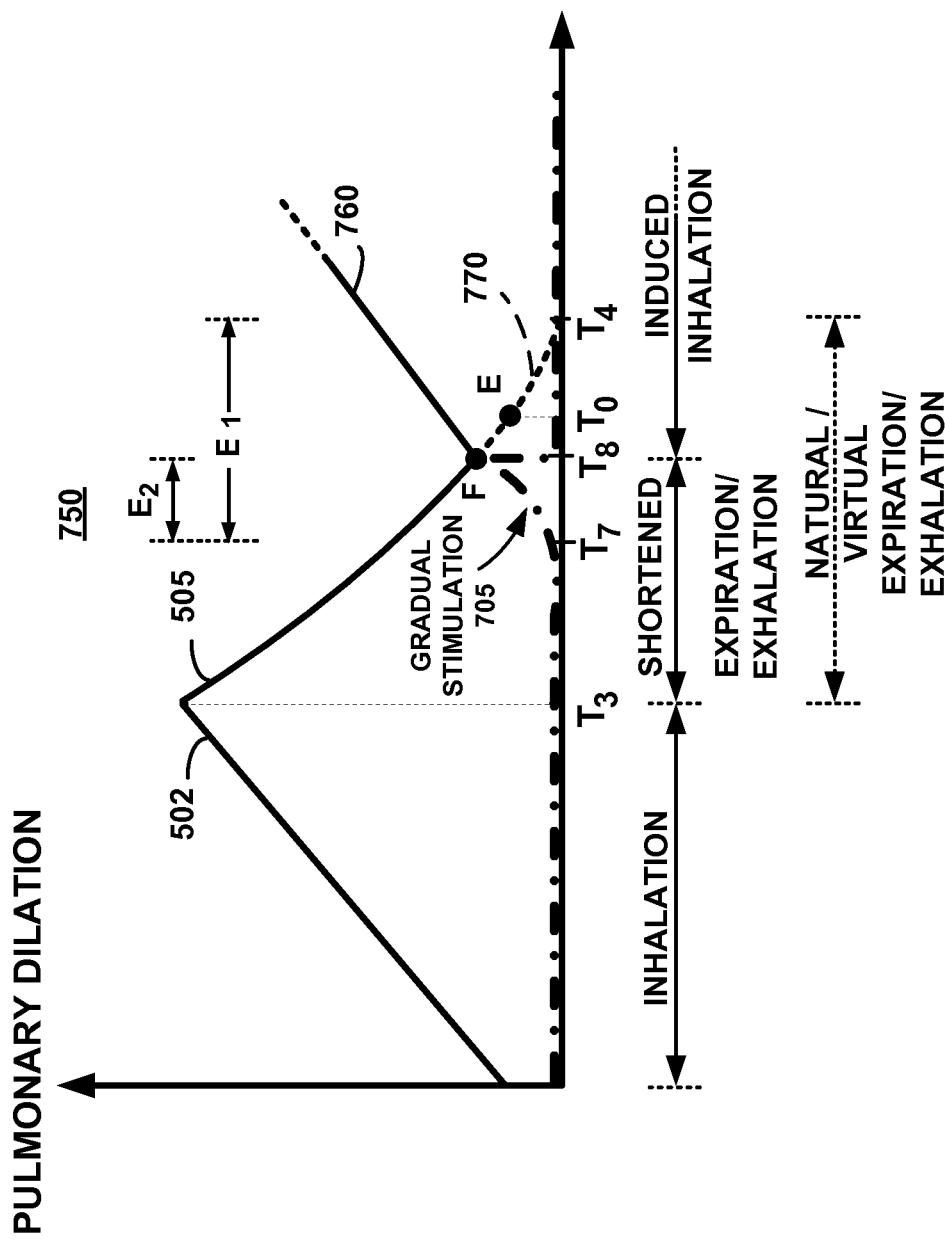

FIG. 7C illustrates yet another graph 750, that is similar to FIG. 7A, wherein the gradual stimulation 705 induces a premature inhalation, or the patient's natural inhalation 760 is initiated on its own, at or around point F (time $T_8$). In which event, the stimulation 705 will no longer be allowed to unnecessarily increase, and will thus be interrupted. The dashed line 770 illustrates the virtual pulmonary (or pharyngeal) dilation, had the inhalation 760 not taken place.

Figure 8:
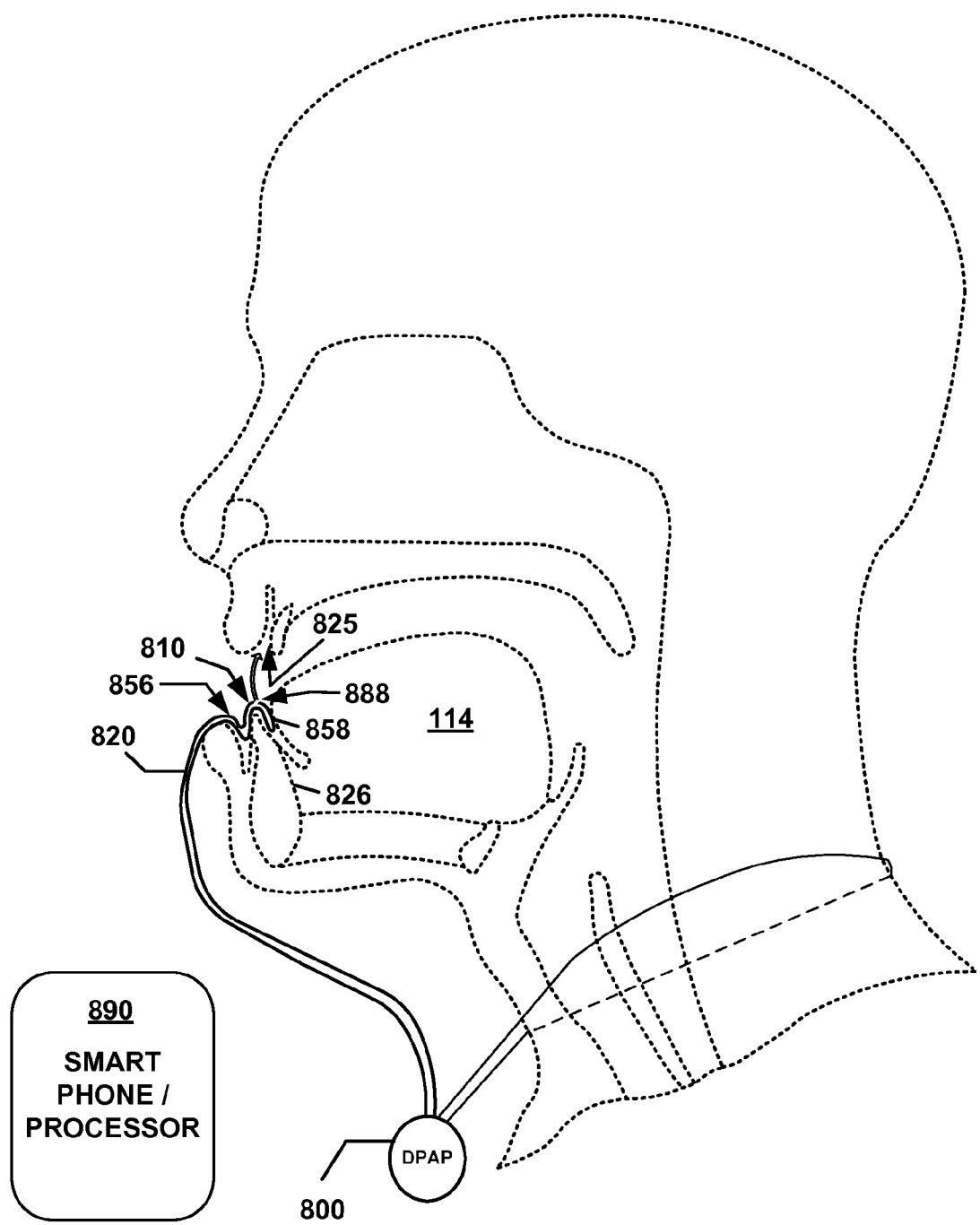
FIG. 8 illustrates another DPAP embodiment according to the present invention, that can be worn by a user, as a necklace, and that uses a dental appliance.

The significant reduction in the power requirement to operate the present DPAP device, enables the miniaturization of the DPAP device to such a size that enables it to be wearable or portable by the user, and not just simply transportable. One such DPAP 800 is illustrated in FIG. 8 that shows the DPAP 800 being worn by a user as a necklace or pendant.

According to a preferred embodiment, the DPAP 800 uses a dental appliance 810 that fluidly communicates with the DPAP 800 by means of an oral tube 820, which delivers the stimulation to the airways or more specifically, as shown in this embodiment, to the user's front mouth, upper gum or teeth 825 (FIG. 8), lower gum or teeth 826 (FIG. 9), or the underside of the tongue 114 (FIG. 9).

In a specific preferred embodiment where the dental appliance 810 is used in conjunction with the oral tube 820 for delivering the intake puff of gas, the dental appliance 810 may be made integrally with, and of the same material as the oral tube 820 for allowing the gas to pass therethrough. The dental appliance 810 includes a formable or compliant section 856 that fits over the user's teeth or gum 825, and an internal extension 858.

The dental appliance 810 includes an opening 888 that enables the stimulation, such as a gas puff, to be nozzled out of the dental applicant 810, directionally, toward the intended target stimulation area. In FIG. 8, the opening 888 is positioned so that the stimulation is directed toward the upper teeth or gum 825.

In this particular embodiment, the DPAP 800 is shown in communication with an external communication device 890, such as a smart phone and/or an external processor over a wireless communication channel, such as Blue Tooth, Wi-Fi, or another available or known wireless protocol. The external communication device 890 provides a variety of functions to the DPAP device 800, including but not limited to processing power for performing calculations, thus reducing the components that would have otherwise been added to the DPAP 800. This will reduce the power consumption of the DPAP 800 as well as its overall weight.

Figure 9A:
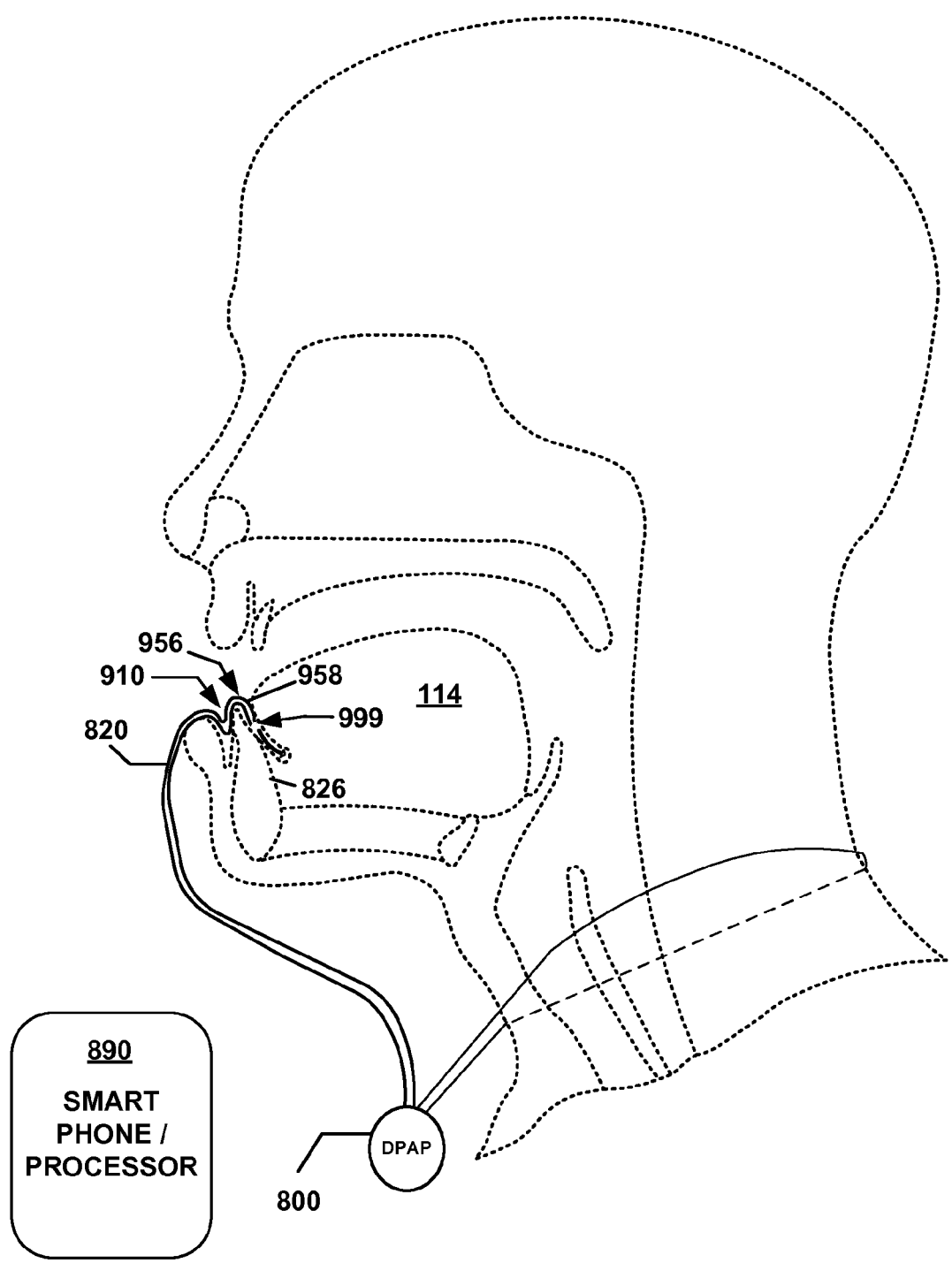
FIG. 9 is comprised of FIGS. 9A, 9B, and 9C, and illustrates the DPAP device of FIG. 8, in use with a variety of dental appliances.

In FIG. 9A, the opening 999 is positioned so that the stimulation is directed toward the lower teeth or gum 826 or the underside of the tongue 114. The dental appliance 910 is used in conjunction with the oral tube 820 for delivering the puff of gas (or stimulation). Similar to the dental appliance 810, the dental appliance 910 may be made integrally with, and of the same material as the oral tube 820 for allowing the gas to pass therethrough. The dental appliance 910 includes a formable or compliant section 956 that fits over the user's teeth or gum 826, and an internal extension 958.

The internal extension 958 includes an opening 999 that enables the stimulation to be nozzled out of the dental applicant 910, directionally, toward the intended target stimulation area, such as the lower teeth or gum 825 or the underside of the tongue 114.

According to yet another embodiment of the present invention, the internal extension 958 or the compliant section 956 may include a combination of nozzles that are positioned to selectively direct and distribute the stimulation to several target regions of the mouth.

Figure 9B:
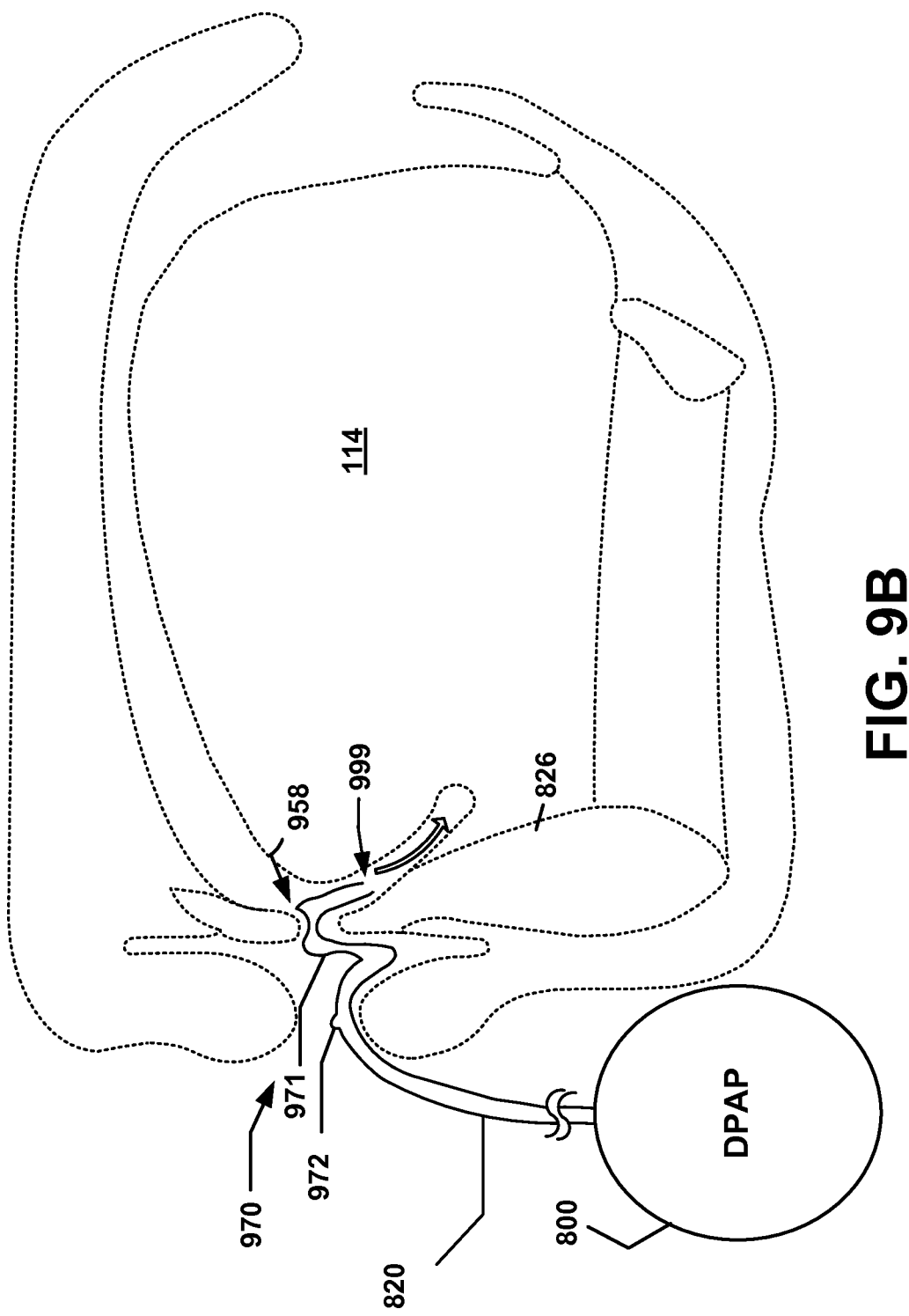
Figure 9C:
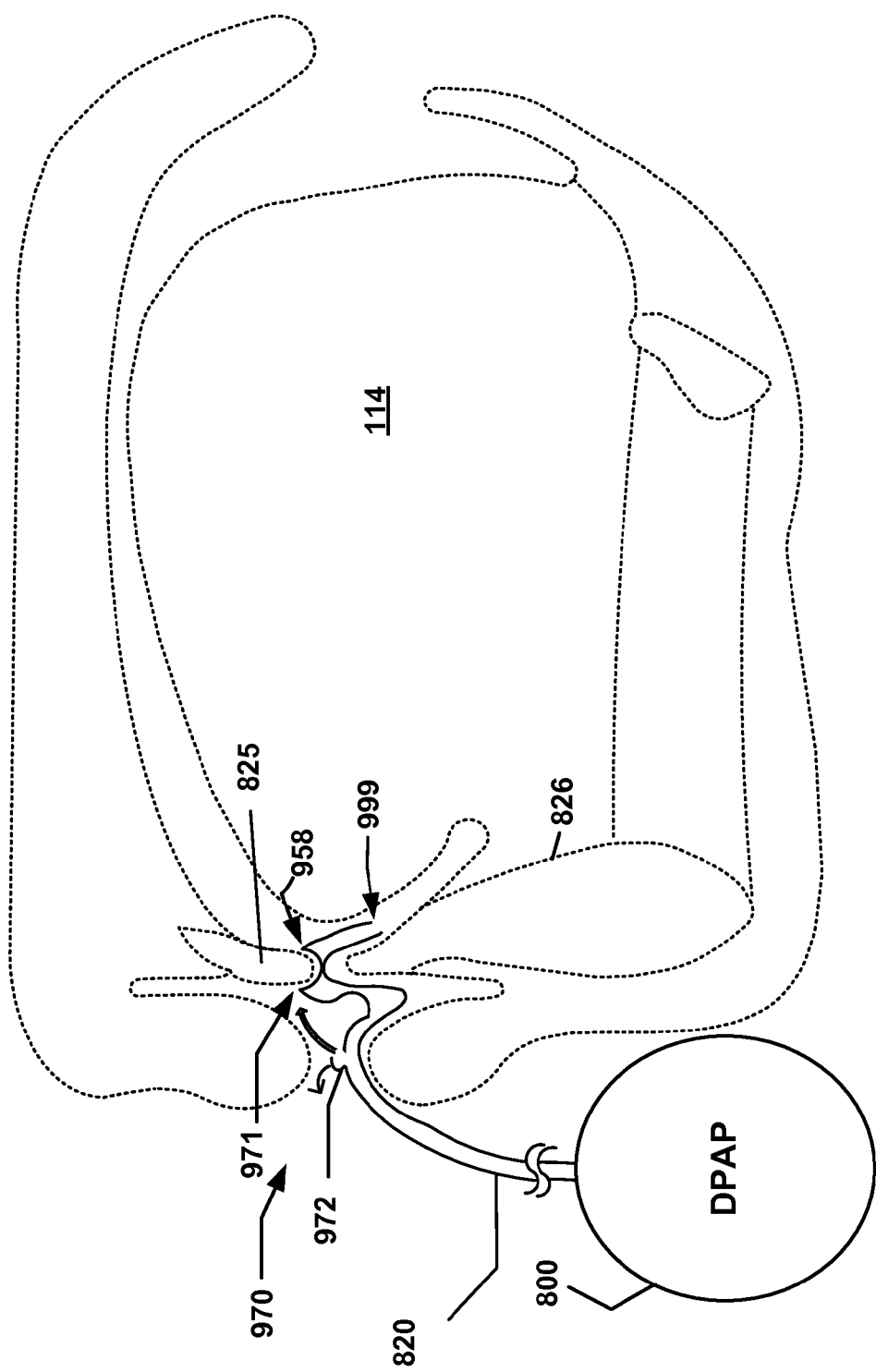

As further illustrated in FIGS. 9B, 9C, the dental appliance 970 presents an additional advantage to the user. The compliant section 971 of the dental appliance 970 includes two additional features. The first feature is a soft or pliable section 958 that fits between the upper and lower teeth 825, 826. During regular breathing events, the teeth 925, 926 slightly pressed against the pliable section 958 and deform it slightly so that it forms a resting seat for the teeth. During regular breathing events, the pliable section of seat 958 does not restrict the flow of fluid within the oral tube 820.

The dental appliance 970 maintains the upper and lower teeth 925, 926, slightly separated. The variation of the thickness of the dental appliance 970 may even provide some repositioning to the jaws to assist in maintaining the airway passages open.

The second feature of the dental appliance 970 is the valve 972 that is preferably positioned on the tube 820 or the compliant section 970. As long as the user does not grind the upper and lower teeth 825, 826, the valve 972 is normally closed, as shown in FIG. 9B.

However, with reference to FIG. 9C, since teeth grinding is believed to be associated with sleep disorder, when the user starts to grind his/her teeth 925, 926, then the grinding motion closes the pliable section of seat 958, and a back-pressure is built within the tube 820. This back pressure (or another feedback) causes the valve 972 to open and to direct the stimulation toward the teeth 825 and/826, as explained earlier. Once the grinding action stops, the flow through the nozzled opening 999 resumes and the valve 972 is closed.

It should be noted that the DPAP 800 can measure the back pressure resulting from the exhalation and from the closure of the pliable section 958, to determine the onset of the exhalation, the stimulation point E, and the delivery and timing of the stimulation.

Figure 10:
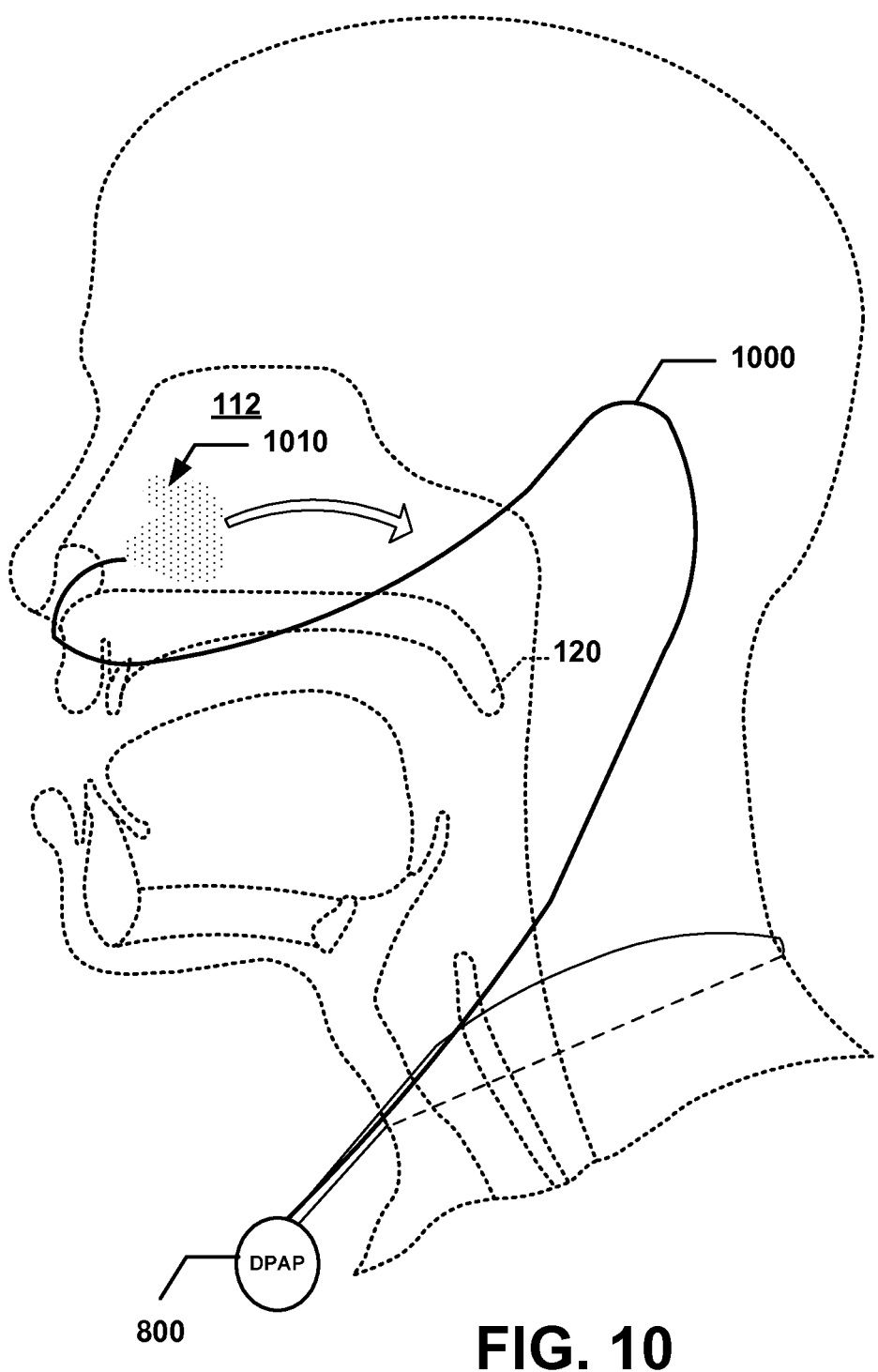
FIG. 10 illustrates the DPAP device of FIG. 8, in use with a nasal tube.

FIG. 10 illustrates the DPAP device 800 of FIG. 8, in use with a nasal tube 1000. The design and operation of the DPAP 800 enables its use with a simple nasal tube 1000 that is currently used in clinics and hospitals. Contrary to the conventional CPAP devices, the nasal tube 1000 does not restrict natural breathing. In other terms, if the DPAP 800 is turned off, the user will still be able to breathe. This is not typically the case with conventional CPAP devices. As a result, the DPAP 800 is a true assist device for breathing in that it selectively supplements natural breathing and does not regulate it completely.

The nasal tube 1000 is typically looped around the user's ears and delivers the stimulation to the nasal cavity 112. As the stimulation, such as a puff of gas enters the nasal cavity 112, it expands and may, in certain events, vaporize into particles 1010. These particles stimulate the user's olfactory senses and cause a reaction of the uvula 120, thus clearing the airways for breathing.

Figure 11:
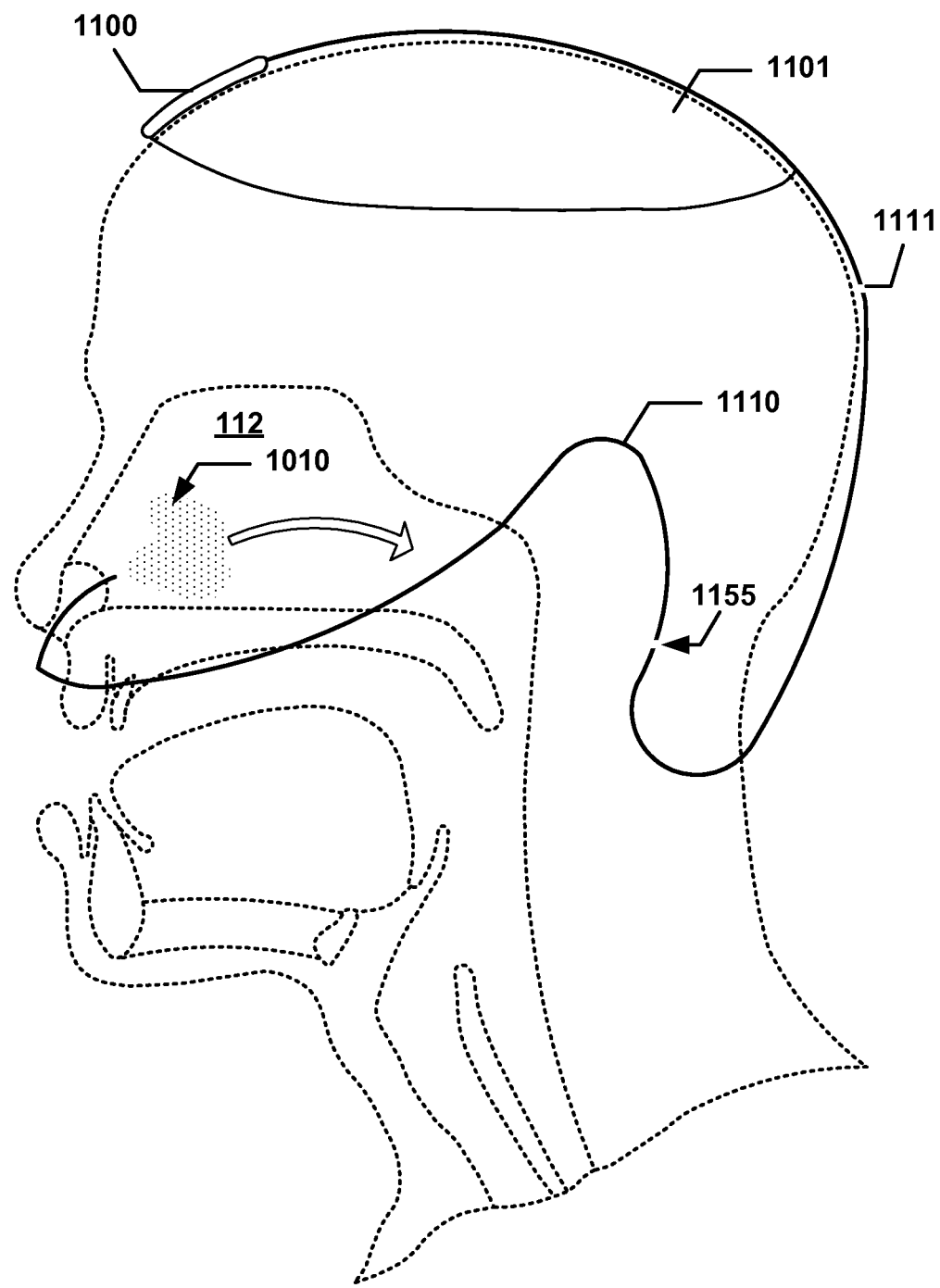
FIG. 11 illustrates the DPAP device of FIG. 8, that can be worn by the user, by means of a head gear.

FIG. 11 illustrates another way of donning the DPAP device 1100. The DPAP 1100 can be worn by the user, by means of a head gear or a strap 1101, and is connected to a nasal tube 1110, as explained earlier. The DPAP device 1100 and the tube 1110 do not interfere with the user's sleep positions, contrary to the conventional tubes that connect the conventional masks to the CPAP devices.

According to another embodiment of the present invention, it would be possible to incite the desired breathing response of a user, by stimulating, for example, the user's ear, the top of the head, or the scalp. The stimulation can be done by means of one or a plurality of holes, openings, or nozzles 1111, along the nasal tube 1110, in order to allow at least some of the stimulation to escape and stimulate the target area or areas.

According to another embodiment, one such opening 1155 is positioned in close proximity to the user's ear or ears, to generate an auditory stimulation, such as a high frequency pitch that causes the desired respiratory response. It would also be possible to pre-train the patient's automatic response to the auditory stimulation, to facilitate the desired response.

Figure 12:
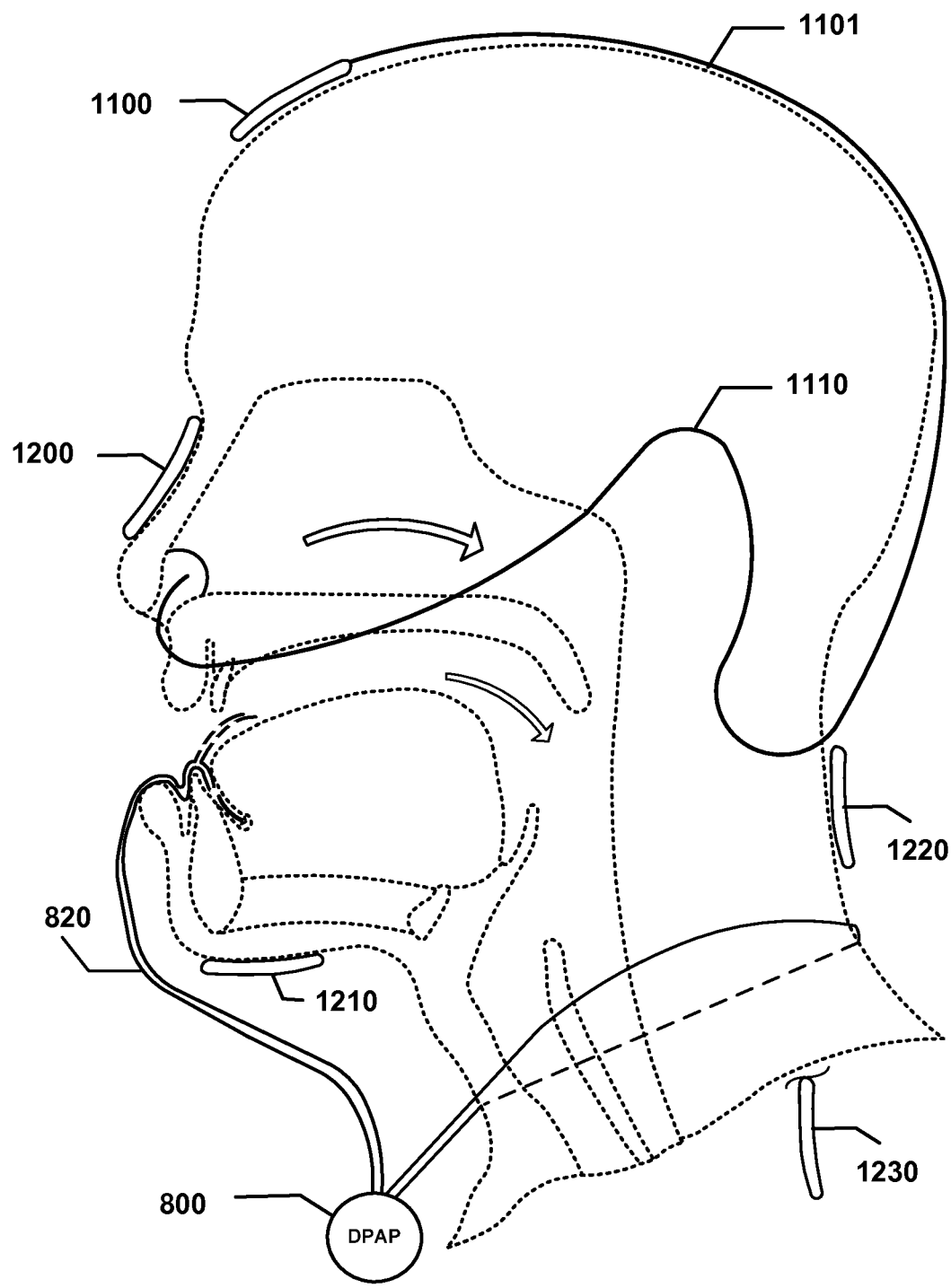
FIG. 12 illustrates a plurality of DPAP devices of FIG. 8, that can be selectively worn by the user.

FIG. 12 illustrates a plurality of DPAP devices of 800, 1100, 1200, 1210, 1220, 1230, that can be selectively worn (one or more) by the user, to effect the desired stimulation at different target areas or sites of the body. While only six exemplary DPAP devices are illustrated herein, it should be clear that a different number of DPAP devices as well as their associated target stimulation areas may be selected to best achieve the desired result. For illustration, the DPAP device 1230 may be worn in proximity to the user's armpit (or another part of the user's body) to provoke a change in the user's posture.

Figure 13:
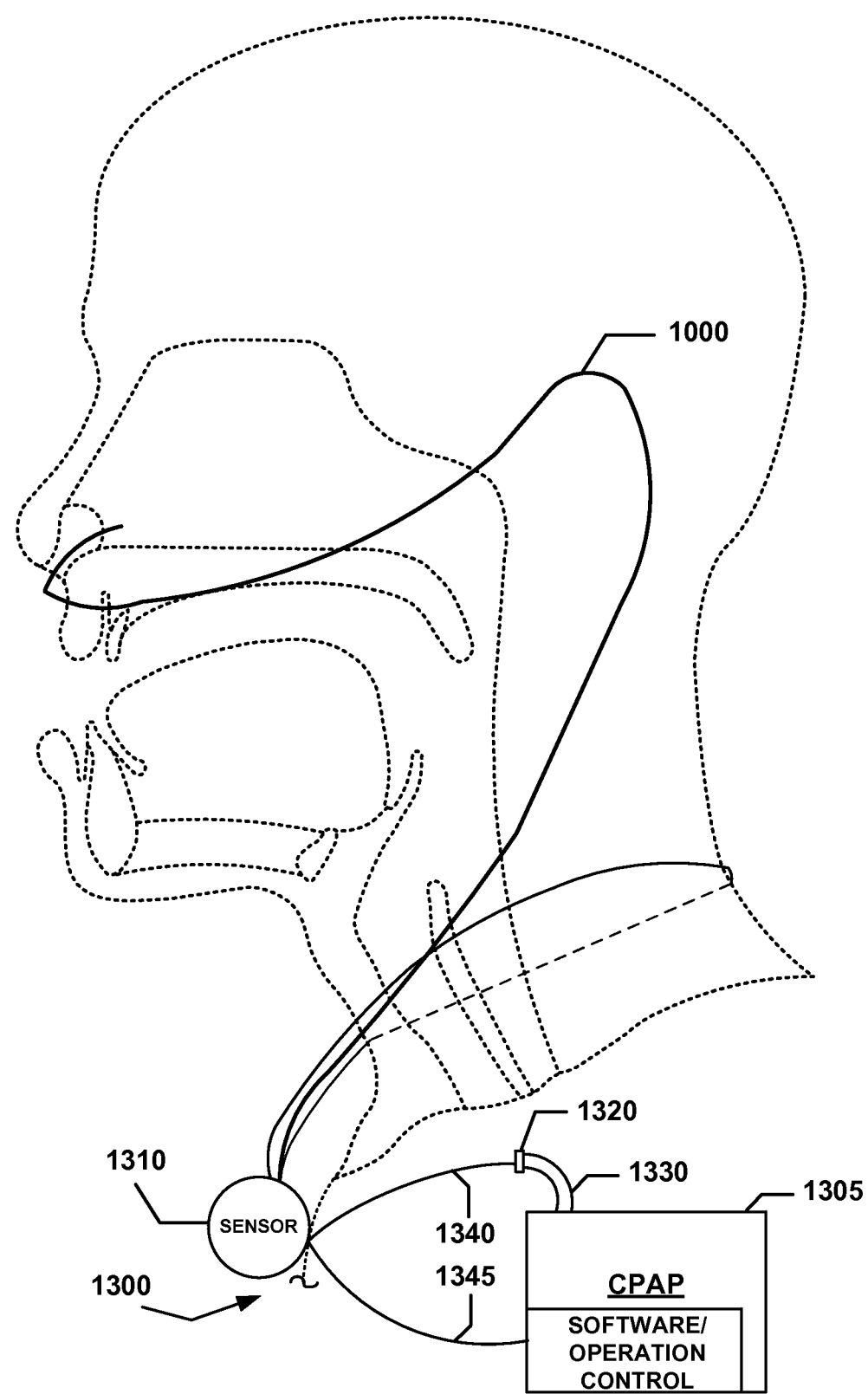
FIG. 13 illustrates another embodiment of the DPAP device according to the present invention, that can be used as a retrofit to an existing CPAP device.
Figure 14:
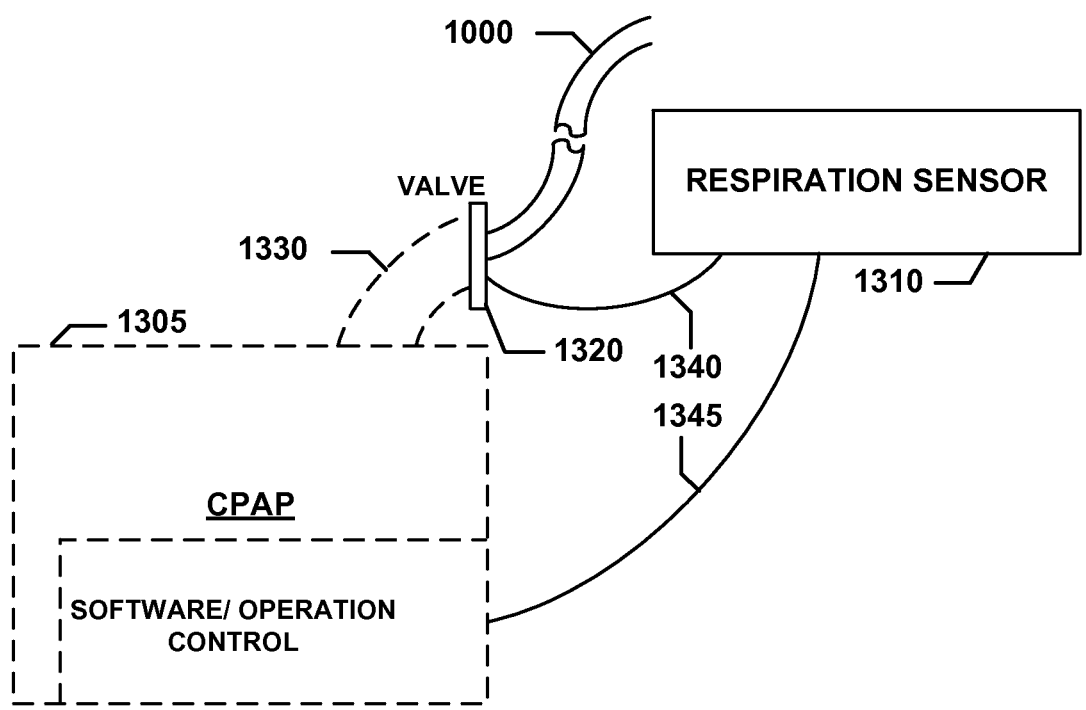
FIG. 14 is a block diagram of the DPAP device of FIG. 13, shown in use as a retrofit to the CPAP device.

FIGS. 13 and 14 illustrate another DPAP device 1300 according to an alternative embodiment of the present invention, which can be used as a retrofit to an existing CPAP device 1305. The operation of an exemplary conventional CPAP device 1305 can be regulated by a software application, with the continuous air being forced out of a hose 1330 that leads to a mask or some other respiration device.

The DPAP device 1300 makes use of the pumping force of the conventional CPAP device 1305. The DPAP device 1300 includes a respiration sensor 1310 that can be worn by the user like a necklace due to its miniaturized size, as explained earlier. The respiration sensor 1300 senses the onset of the exhalation stage and the approach of the stimulation point, E.

For example, the respiration sensor 1310 can measure the back pressure resulting from the user's exhalation (or the chest movement) to determine the onset of the exhalation stage and to monitor the exhalation stage, in order to determine (or to have the CPAP software determine) or calculate the optimal stimulation point, E.

To this end, the sensor 1310 is connected to the nasal tube 1000 and is also connected to a valve 1320 via a fluid tube 1340. The valve 1320 controls the flow of air from the CPAP device 1305 so that the DPAP device 1300 operates similarly to the DPAP 800, as explained earlier. The valve 1320 is connected at its other end, to the hose 1330. The valve 1320 can include a flow reducer that controls the rate of flow, the volume, and the pressure of the stimulation.

According to another design, the sensor 1310 is connected to the control circuitry of the CPAP device 1305 by means of wiring 1345 (or wirelessly by means of an interface). Alternatively, the operation of the CPAP device 1305 can be reprogrammed by the manufacturer (or a different authorized provider) to respond to the sensor 1310 and to operate the CPAP device 1305 according to the teachings of the present invention.

Figure 15A:
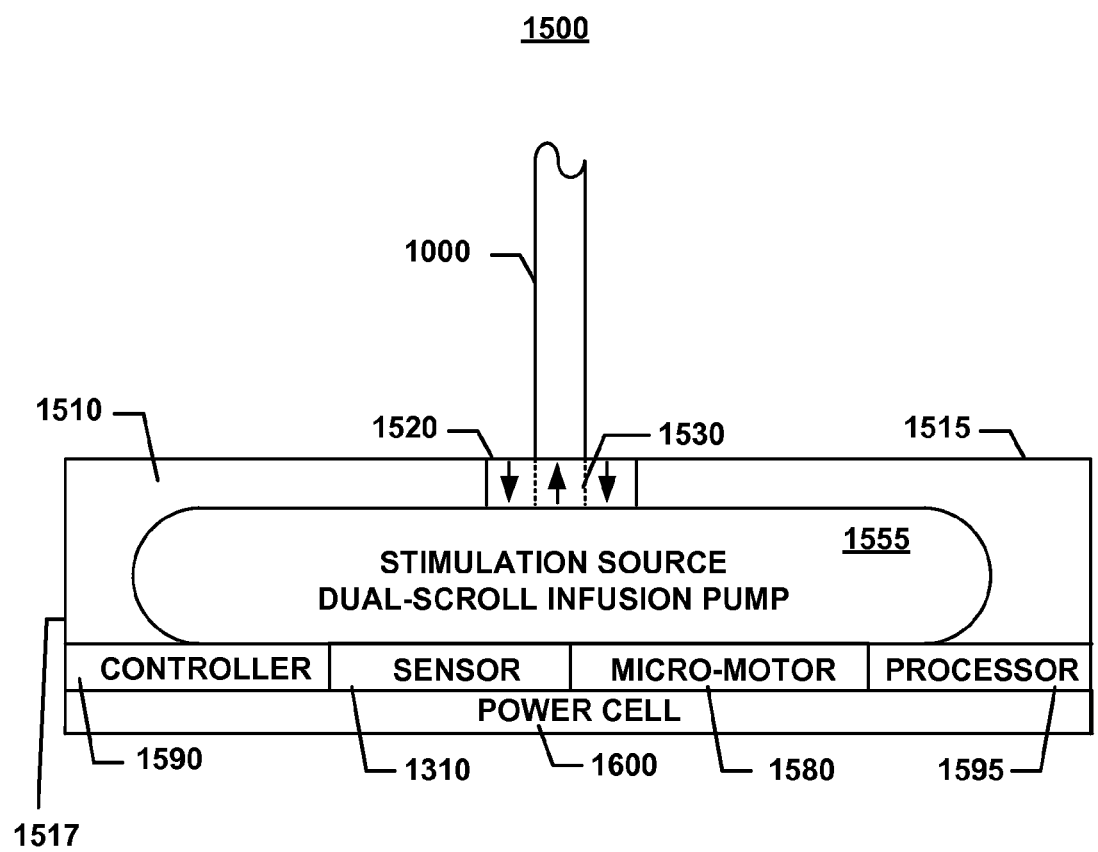
FIG. 15A is a block diagram architecture of a DPAP device according to a preferred embodiment of the present invention, shown using a dual-spiral infusion pump.

FIG. 15A is a block diagram architecture of a DPAP device 1500 (or of the DPAP device 800) according to a preferred embodiment of the present invention. The DPAP device 1500 generally includes a housing 1510 having a top side (or top cover) 1515. As used herein, the directional terms "top," "bottom," or other similar terms, are not intended to limit the use of the DPAP device e.g., 800, 1500 in a directional manner, but are rather used for illustration purposes, to facilitate the description of the present invention.

The DPAP device 1500 further includes an infusion pump 1555 with one or more inlet port 1520 and one or more outlet port 1530, that permit the exchange of fluid through the top side 1515. It should however be clear that while the inlet port 1520 and the outlet port 1530 are shown as being accessed from the top side 1515, other designs might be optimized by accessing the inlet port 1520 and the outlet port 1530 from the lateral side 1517 (or another side) of the housing 1510.

Figure 15B:
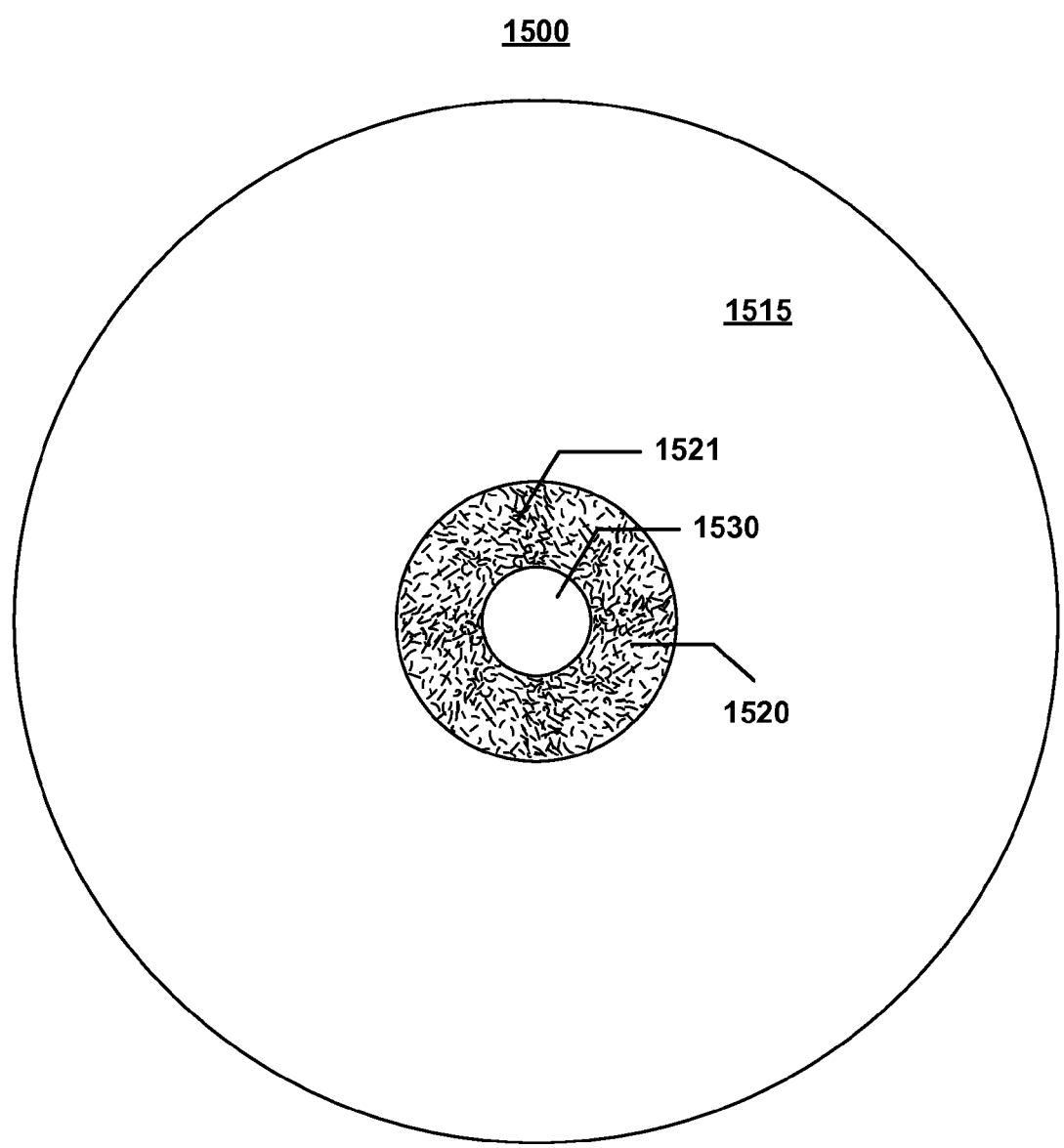
FIG. 15B is a top view of the DPAP device of FIG. 15A.

As further illustrated in FIG. 15B, the inlet port 1520 and the outlet port 1530 are concentric with a circular (or a different appropriate shape) cross-section. The inlet port 1520 may be covered by a filter 1521 that filters the incoming air or gas. The outlet port 1530 is connected to the nasal tube 1000.

In this particular embodiment, the infusion pump 1555 is the stimulation source that generates the stimulation, such as an air (a fluid, gas, or a combination of a gas and liquid) puff. The inlet port 1520 allows air (or gas) to be introduced into the infusion pump 1555, while the outlet port 1530 allows the pressurized air to be nozzled out of the infusion pump 1555 to provide the desired stimulation, as explained herein.

In one specific embodiment, the infusion pump 1555 is a dual-spiral infusion pump, as described in more detail in U.S. Pat. No. 5,578,077 to Kassatly. It should however be understood that different miniaturized pump may alternatively be used. The infusion pump 1555 is housed inside the housing 1510.

Another important feature of the DPAP device 1500 of the present invention, is the power cell 1600, which will be explained later in more detail. The power cell 1600 is preferably self rechargeable, and powers the various electrical and electronic components of the DPAP 1500, such as the respiration sensor 1310, a micro-motor 1580, a controller 1590, and a processor 1595.

The micro-motor 1580 is coupled to the infusion pump 1555 and causes its spiral-shaped scrolls to rotate. The controller 1590 regulates the flow of air and the delivery timing of the stimulation. The processor 1595 performs the necessary computations and is programmable. It should be understood that, in order to reduce the power consumption of the DPAP device 1500, the processor 1595 could be done externally or remotely, such as by means of a smart phone/processor 890 (FIG. 8).

Figure 16:
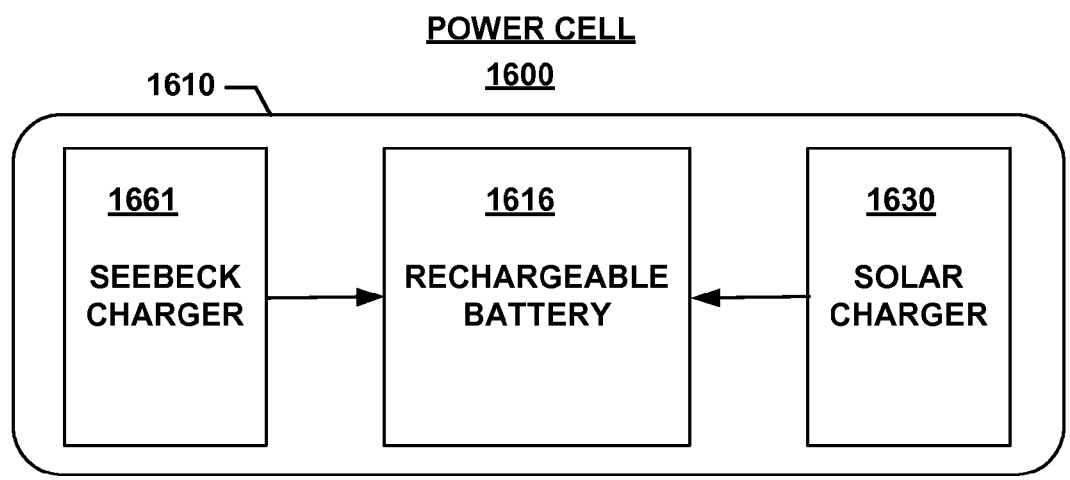
FIG. 16 is a block diagram of a power cell that forms part of the DPAP device of FIG. 15A.

FIG. 16 is a block diagram of the power cell 1600 that forms part of the DPAP device 1500 of FIG. 15A, according to a preferred embodiment of the present invention. The power cell 1600 generally includes a rechargeable battery 1616, of the type that is known or available. The rechargeable battery 1616 is automatically charged by one or more charging devices.

In the exemplary embodiment of FIG. 16, the rechargeable battery 1616 is shown as being charged by two charging devices, a Seebeck charger 1661 and a solar charger (or a light/photon charger) 1630. It should be understood that other chargers may alternatively be used, including but not limited to an external charger that charges the rechargeable battery 1616 directly.

In the embodiment illustrated in FIGS. 15A and 16, the micro-motor 1580 is preferably a thermoelectric micro-motor that is powered by the thermoelectric effect. The thermoelectric effect is also referred to as the Seebeck effect, and is used to generate electricity. Generally, the thermoelectric effect encompasses three separately identified effects: the Seebeck effect, the Peltier effect, and the Thomson effect.

In general, a thermoelectric device includes one or a series of p-type semiconductor elements and one or a series of n-type semiconductor elements that are electrically connected. When the two dissimilar elements are subjected to different temperatures, the Seebeck effect causes a voltage to be generated across the junctions between the p-type and n-type semiconductor elements.

The solar charger 1630 can further heat the Seebeck elements of the Seebeck charger 1661, to generate additional temperature differential that causes the Seebeck charger 1661 to generate electricity for charging the rechargeable battery 1616.

FIG. 15B shows the DPAP device 1500 as having a cylindrical shape with a circular top side 1515. This exemplary top side 1515 accommodates the inlet port 1520 and the outlet port 1530. The inlet port 1520 and the outlet port 1530 are concentric, but they can assume other positions and shapes. As illustrated in FIG. 15A, the outlet port 1530 is connected to the nasal tube 1000, while the inlet tube can preferably be capped with a filter 1521 that captures undesirable particles.

Figure 17:
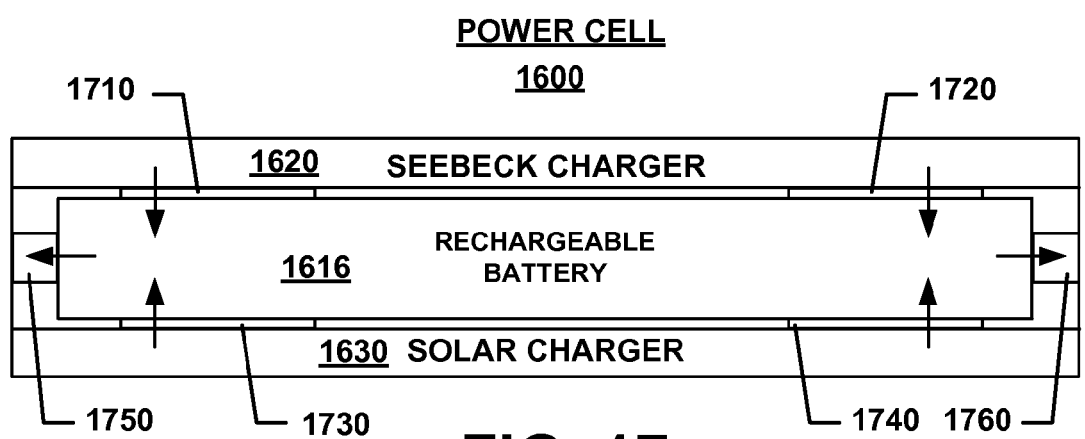
FIG. 17 is another block diagram of the power cell of FIG. 16, showing the layout of two different chargers and a rechargeable battery, wherein the power cell can be used as an accessory to the DPAP device of the present invention, or it can be used independently with a variety of other devices.

FIG. 17 is another block diagram of the power cell 1600 of FIG. 16, showing the layout of two different chargers 1620, 1630 and the rechargeable battery 1616. The power cell 1600 can be used as an accessory to the DPAP device 1500 of the present invention, or it can be used independently with a variety of other devices.

In this specific exemplary embodiment, the rechargeable battery 1616 of the power cell 1600 is placed centrally, and is electrically connected to the Seebeck charger 1620 by electrical contacts 1710, 1720. The rechargeable battery 1616 is also electrically connected to the solar charger 1630 by means of electrical contacts 1730, 1740. Additional electrical contacts, connect the rechargeable battery 1616 to other components of the DPAP device 1500, including but not limited to the controller 1590, the micro-motor 1580, and the processor 1595.

The power cell 1600 may be used independently of the DPAP devices of the present invention, and due to its miniaturized size and effectiveness, it can be used to power various electrical and electronic devices. As an example, the power cell 1600 can be miniaturized to power nano devices, whether or not they are implantable or introducible inside the body.

Figure 18:
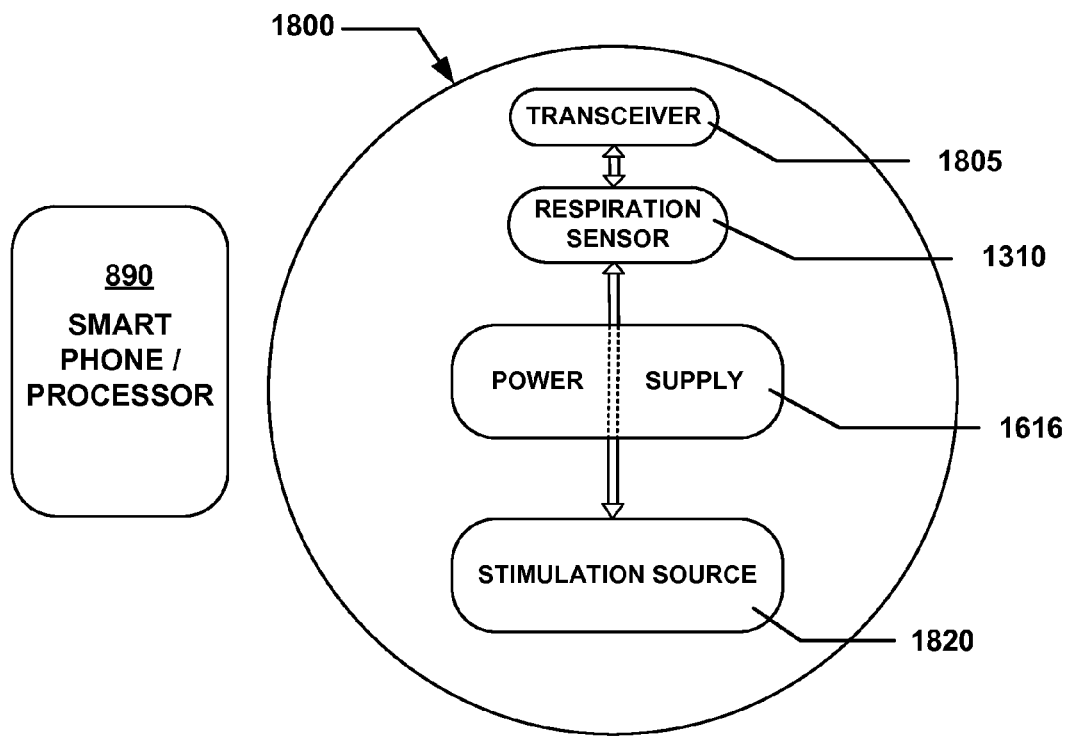
FIG. 18 is a high level architecture of a DPAP device shown in use with a smart phone and/or an external processor, according to the present invention.

FIG. 18 illustrates a DPAP device 1800 in use with a smart phone and/or an external processor 890. To this end, the DPAP device 1800 includes the power supply 1616 that supplies the necessary power to a stimulation source 1820, a respiration sensor 1310, and a transceiver 1805.

Figure 19:
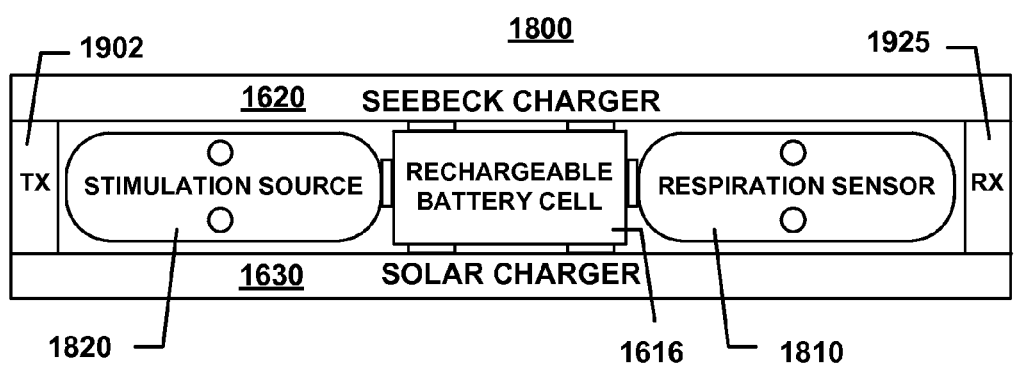
FIG. 19 is a more detailed architecture of the DPAP device of FIG. 14, illustrating two distinct power chargers.

As further illustrated in FIG. 19, the transceiver 1805 includes a transmitter 1902 and a receiver 1925. FIG. 19 further illustrates the stimulation source 1820 as including, for illustration purpose only, the Seebeck charger 1620 and the solar charger 1630.

In use, the DPAP device 1800 is worn by the user as a necklace, with the Seebeck charger 1620 in contact with the user's skin, whether with or without a electrolytic gel. The user's body temperature will raise and sustain the temperature of the Seebeck charger 1620 for generating charging power to the rechargeable battery 1616. The solar charger 1630 further supplements the charging of the rechargeable battery 1616.

When the DPAP device 1800 is not in use, it can be placed on a separate, external charging dock or station 2002, as it will now be described in connection with the DPAP device 2000 of FIG. 20.

Figure 20:
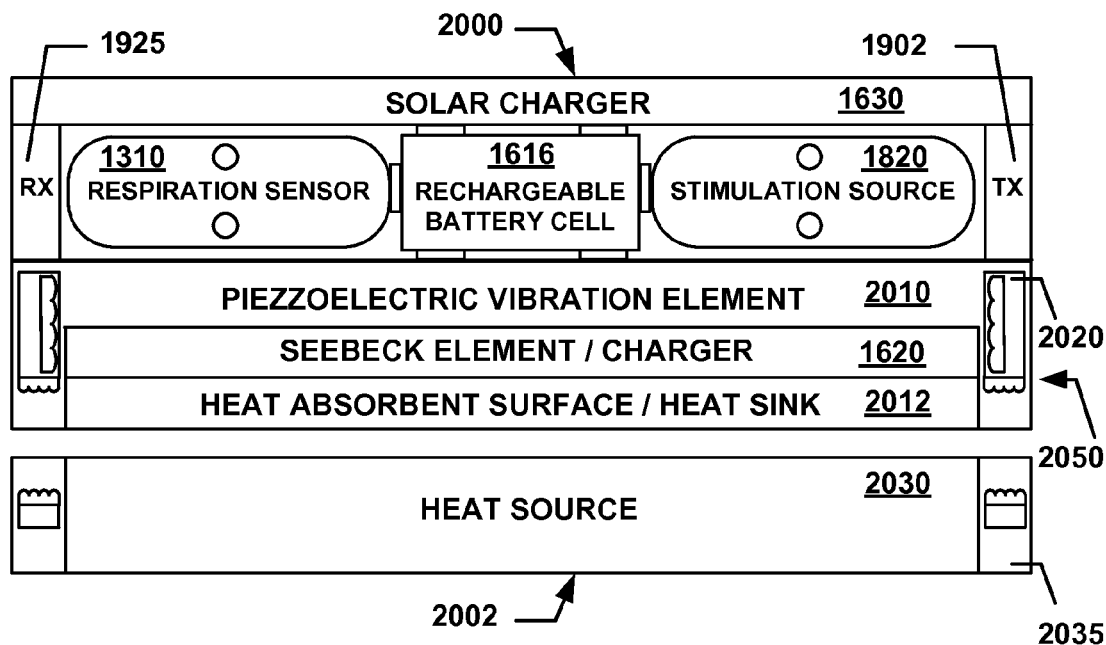
FIG. 20 is a block diagram of the DPAP of the present invention, which includes another embodiment of the power cell, shown docked on an external charging station.

FIG. 20 illustrates the DPAP device 2000 docked on the external charging station 2002. The external charging station 2002 may also be used with the DPAP device 1800 of FIGS. 18 and 19 and the other DPAP devices of the present invention.

The DPAP device 2000 is generally similar in function and design to the DPAP device 1800, but it further includes an additional charging element, namely the piezoelectric vibration element 2010. The piezoelectric vibration element 2010 converts the vibrations of the DPAP device 2000 into electrical current that further charges the rechargeable battery 1616. The vibration frequency of the piezoelectric vibration element 2010 can be set to a predetermined resonance frequency that maximizes the resonance, and thus maximizes the energy conversion from vibration to electrical (or vice versa as needed). As an example, the piezoelectric vibration element 2010 can be tuned to resonate at the user's heart rate, and therefore the piezoelectric vibration element 2010 becomes sensitive to, and captures the heart vibrations. In one embodiment, the piezoelectric vibration element 2010 can generate several milliwatts of power.

The DPAP device 2000 further includes a heat absorbent surface or heat sink 2012 that absorbs the heat from a heat source 2030 of the heat source 2002.

The DPAP device 2000 may further be provided with an inductive element 2020, that extends circumferentially, within and along the periphery of the DPAP device 2000. The inductive element 2020 inductively interacts with a similarly and generally oppositely situated inductive element 2035, to provide vibration to the piezoelectric vibration element 2010, heat to the Seebeck charger 1620, and wherein excess heat is absorbed by the heat absorbent surface 2012, thus minimizing energy loss.

In use, the DPAP device 2000 is placed atop the docking station 2002, such that the heat source 2030 faces the heat absorbent surface 2012, and the inductive element 2035 faces the inductive element 2020 of the DPAP device 2000. The docking station 2002 is generally cylindrically shaped with horizontal dimensions that substantially match those of the DPAP device 2000.

The piezoelectric vibration element 2010, the Seebeck element 1620, the heat absorbent surface 2012, the inductive element 202, and in certain designs, the solar charger 1630, are collectively referred to as power cell 2050.

Figure 21:
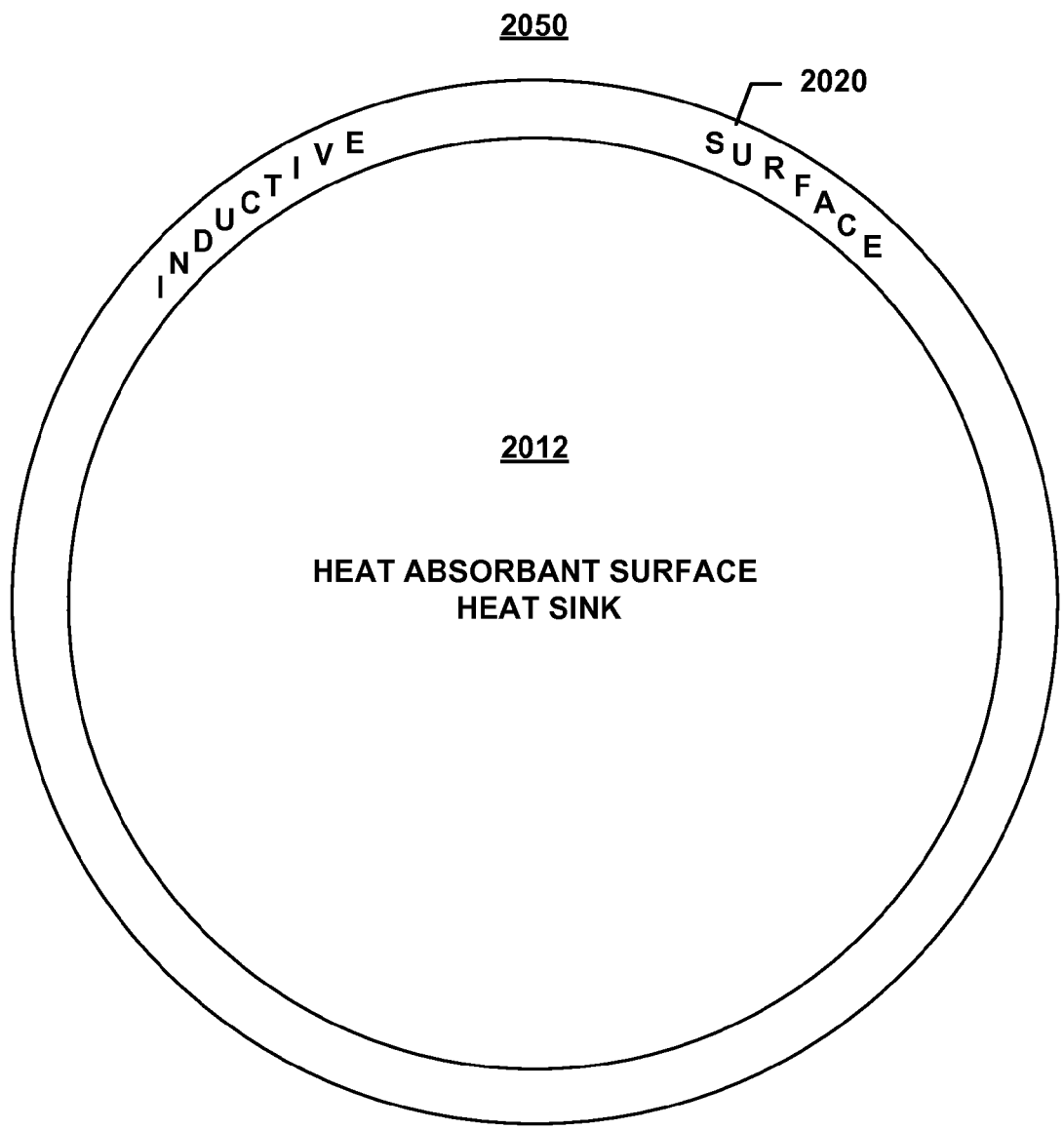
FIG. 21 is a bottom view of the power cell of the DPAP of FIG. 20.
Figure 22:
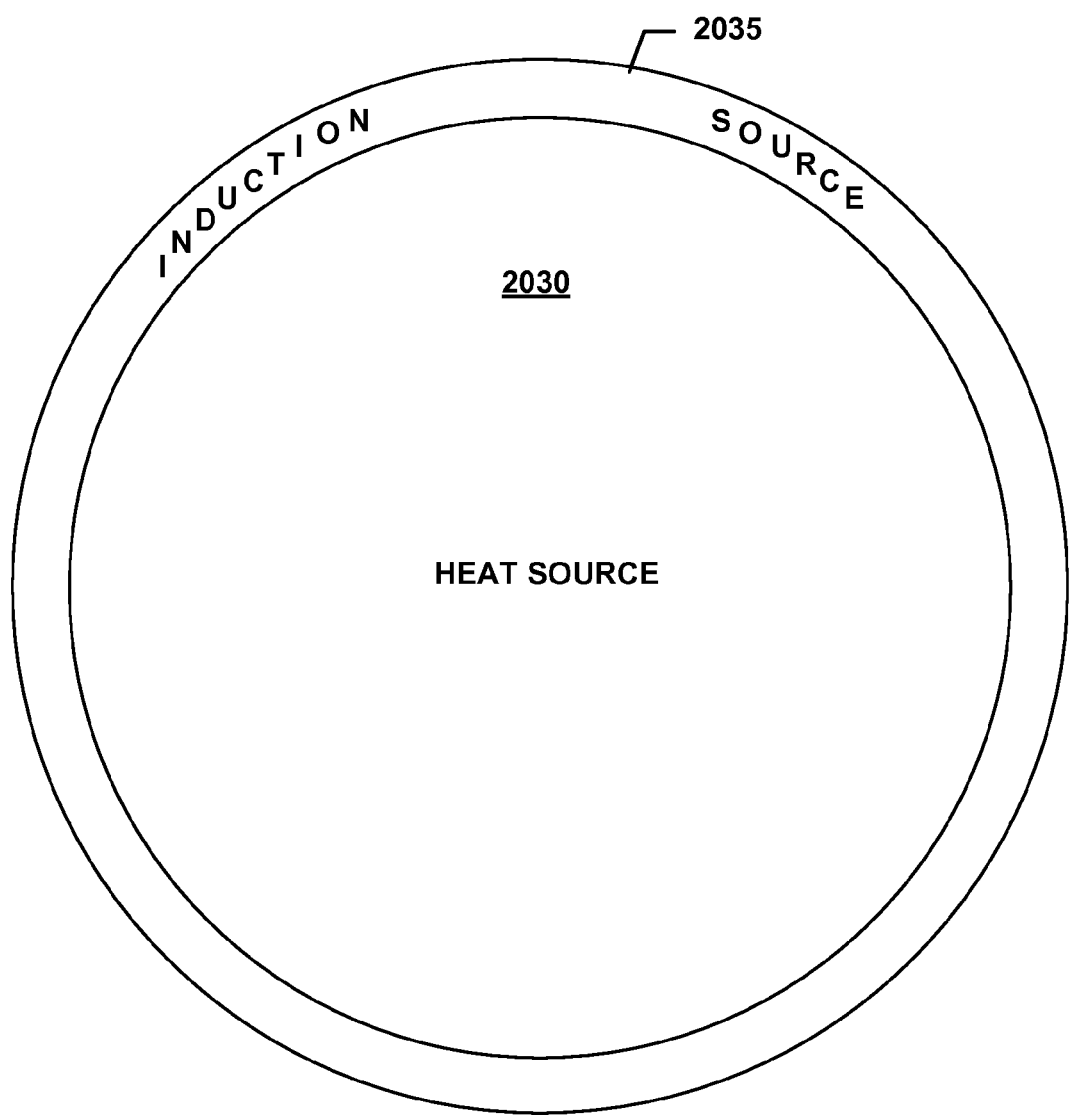
FIG. 22 is a top view of the external charging station of FIG. 20.

FIG. 21 is a bottom view of the power cell 2050 of the DPAP 2000 of FIG. 20. FIG. 22 is a top view of the external charging station 2002 of FIG. 20.

Figure 23:
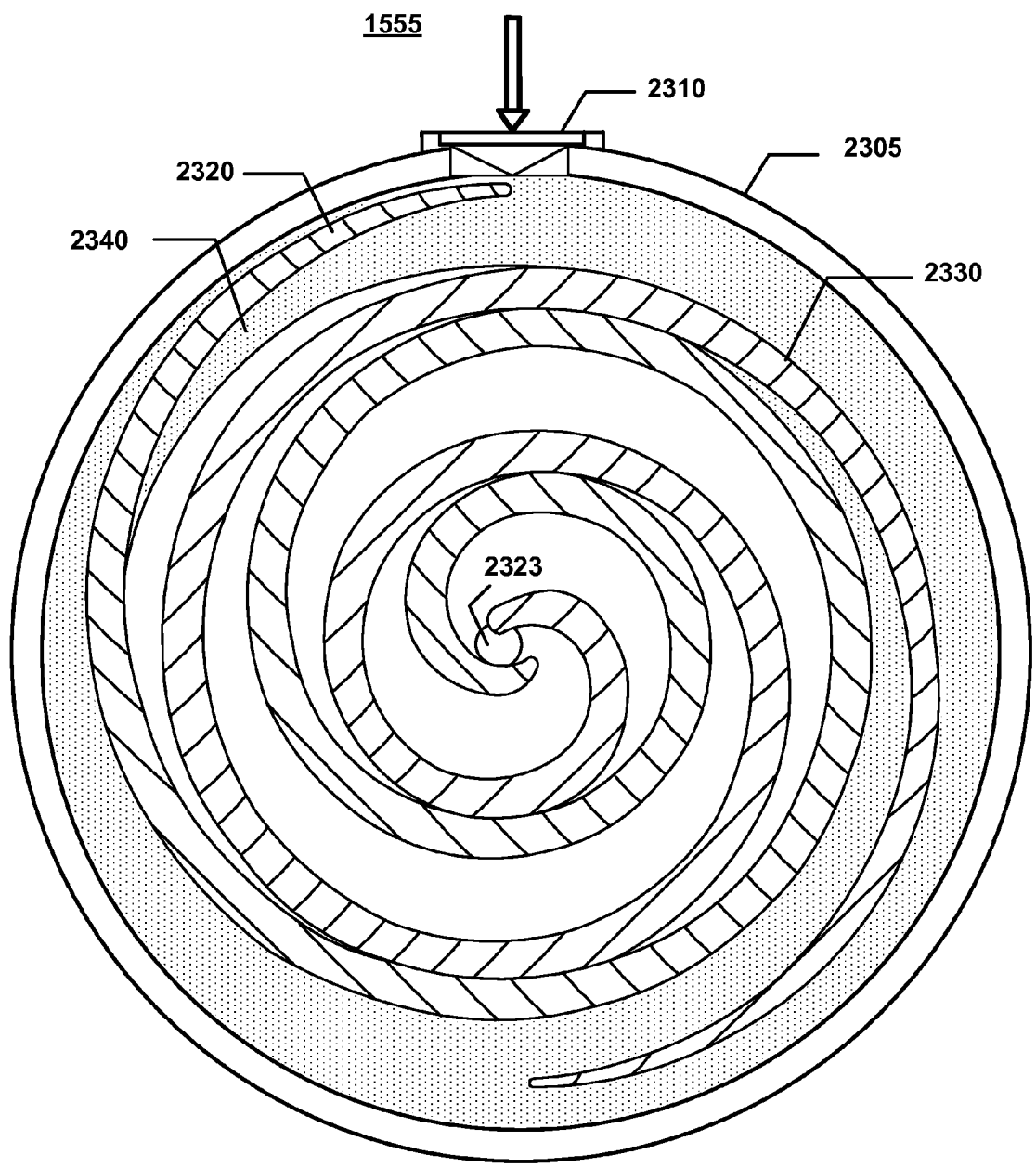
FIG. 23 is a cross-sectional view of the dual-spiral infusion pump of FIG. 15A, showing the air (or another gas) supply being pulled in between the two scrolls of the infusion pump.

FIG. 23 is a cross-sectional view of an exemplary stimulation device of FIG. 15A, which comprises a dual-spiral infusion pump 1555. The infusion pump 1555 intakes air (or another gas) supply through an intake port or valve 2310, inside a body 2305, through two scrolls 2320, 2330. As stated earlier, the operation of the dual-spiral infusion pump 2300 in compressing or expanding a fluid 2340 is explained in more detail in U.S. Pat. No. 5,578,077 to Kassatly, which is incorporated herein by reference in its entirety.

Figure 24:
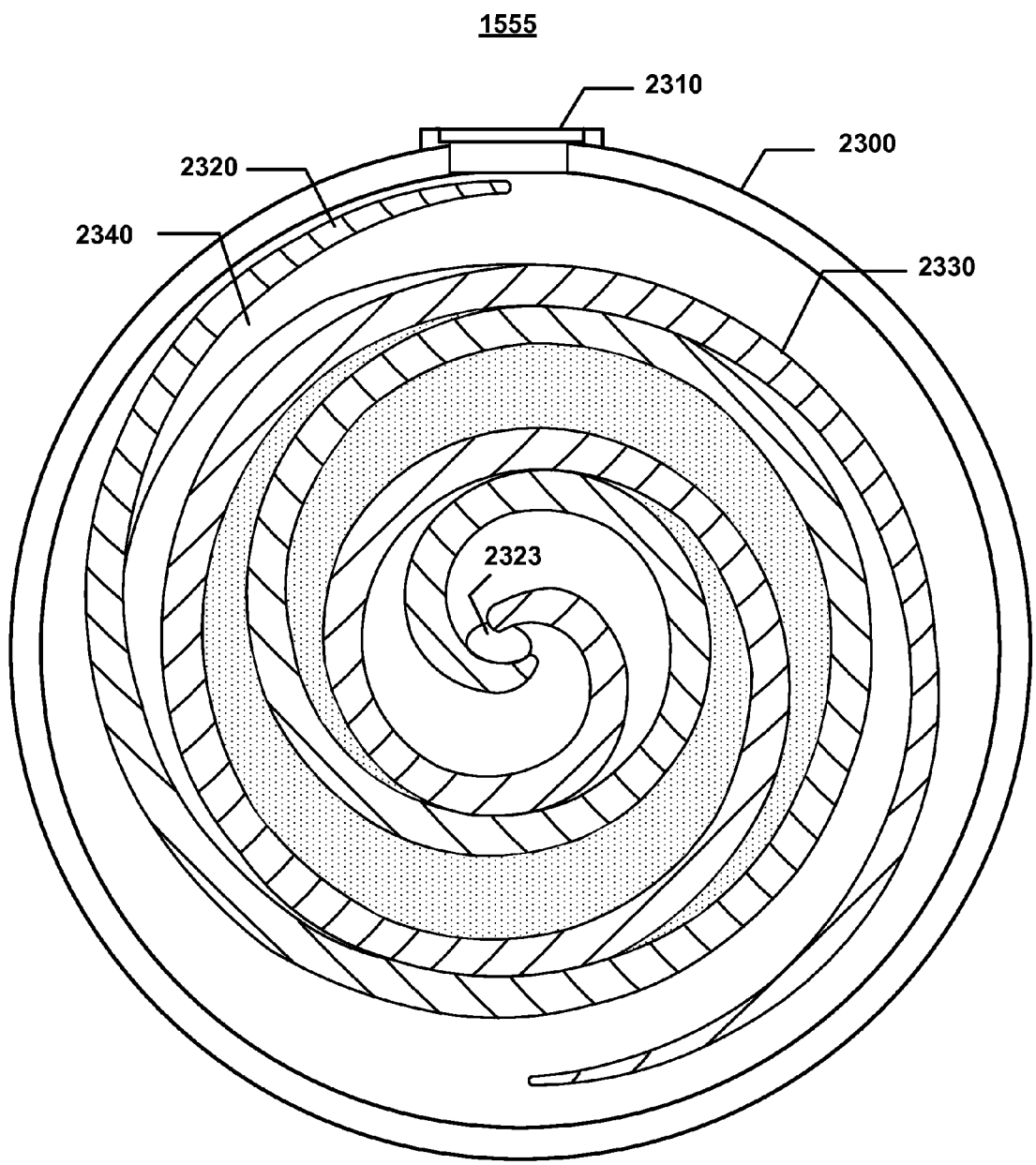
FIG. 24 is a cross-sectional view of the dual-spiral infusion pump of FIGS. 15 and 23, showing the air supply that has been previously introduced in FIG. 23 being compressed, in preparation for release as a stimulation (or excitation) at the excitation point, E.

FIG. 24 is another cross-sectional view of the dual-spiral infusion pump 1555 of FIG. 23, showing the air supply that has been previously introduced in FIG. 23 being compressed, in preparation for release as a stimulation (or excitation) at the excitation point, E, through an output port 2323. As shown in FIG. 15A, the output port 2323 is connected through port 1530, to the nasal tube 820.

Figure 25:
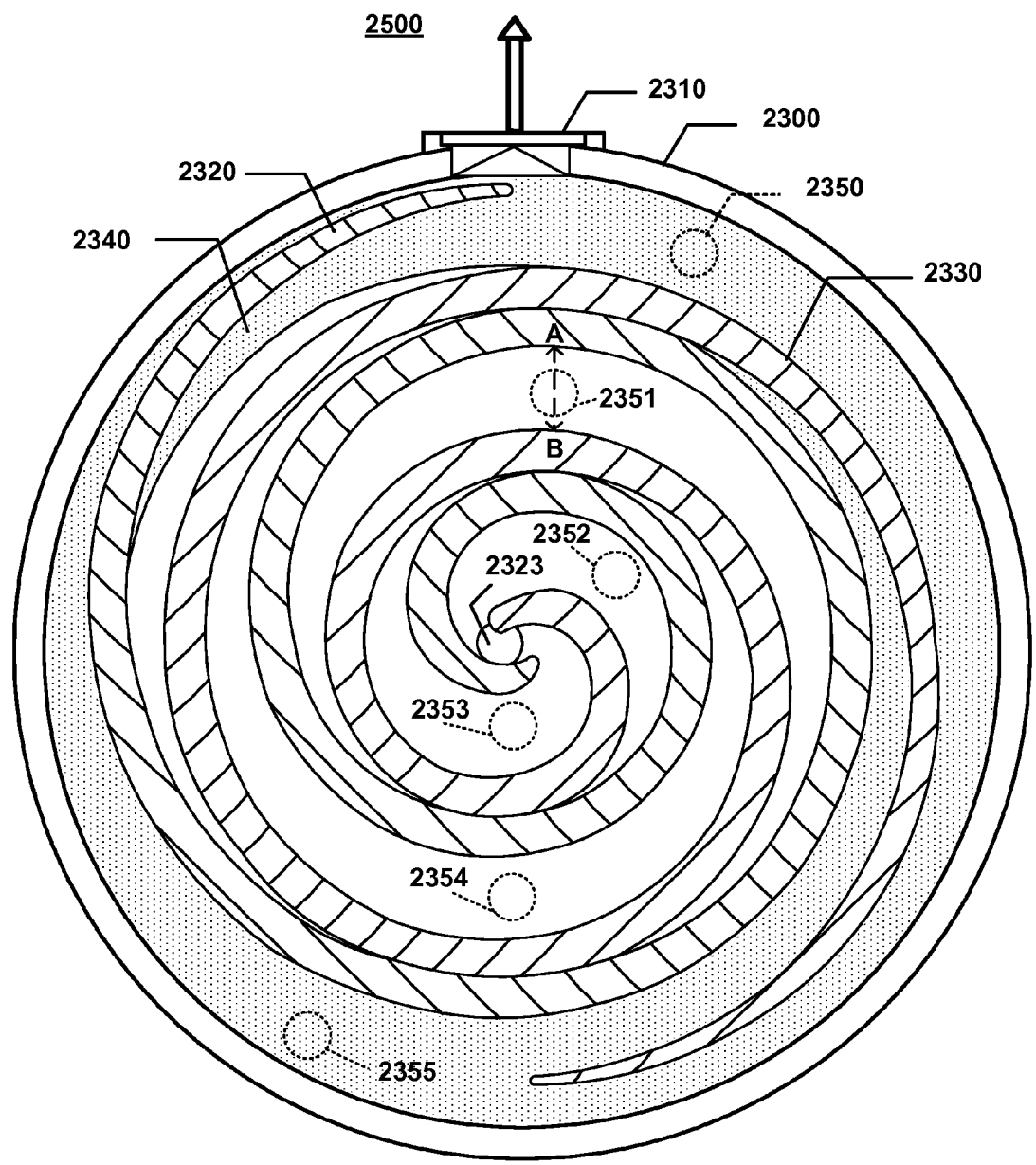
FIG. 25 is a cross-sectional view of an expansion pump comprising a plurality of exhaust ports or valves that allow the expanding fluid to be forced out of the expansion pump.

FIG. 25 is a cross-sectional view of an expansion pump 2500, having basically the same or similar components as those of the dual-spiral infusion pump 1555 of FIGS. 23 and 24, and further comprising a plurality of exhaust ports or valves 2350, 2351, 2352, 2353, 2354, 2355 that are distributed at predetermined locations so as to allow the expanding fluid 2340 to be forced out of the expansion pump 2500.

To this end, the fluid 2340 is inputted through the port 2323, and the relative motion of the scrolls 2320, 2330 is the reverse of that of the corresponding scrolls 2320, 2330 of the spiral infusion pump 1555 of FIGS. 23 and 24. Alternatively, the exhaust ports 2350, 2351, 2352, 2353, 2354, 2355 are omitted and the fluid 2340 is allowed to exhaust through the port or valve 2310. While only six exhaust ports 2350, 2351, 2352, 2353, 2354, 2355 are illustrated, it should be clear that a different number of exhaust ports may be selected.

In one embodiment, the positioning of the exhaust ports 2350, 2351, 2352, 2353, 2354, 2355 is such that they are located at the maximal distance between the two scrolls 2320, 2330, as shown by the double arrow "AB" relative to the exhaust port 2351.

Figure 26:
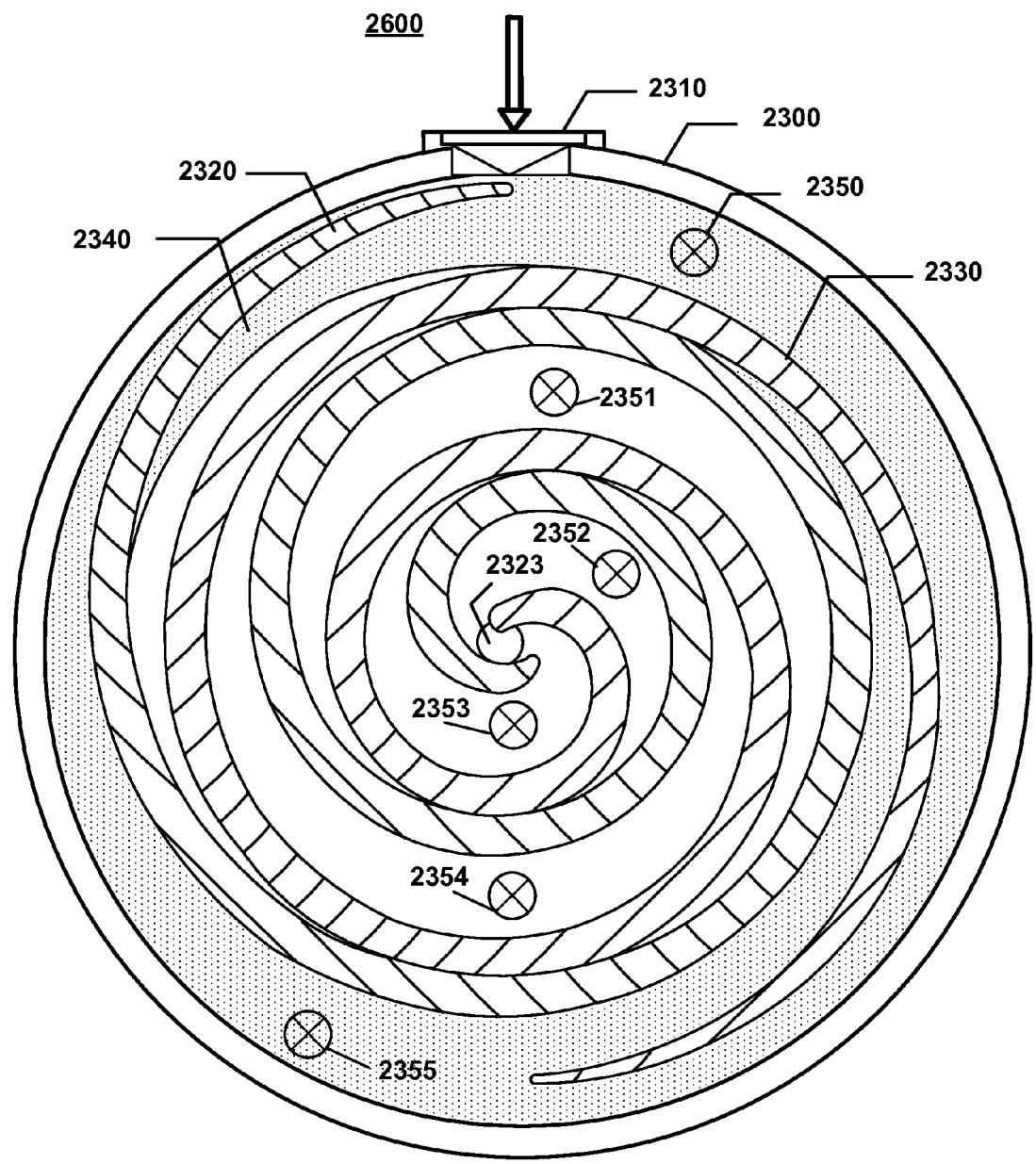
FIG. 26 is a cross-sectional view of a dual function infusion/expansion pump having basically the combined function of the dual-spiral infusion pump of FIGS. 23 and 24, and that of the expansion pump 2500 of FIG. 25, for use as a breathing assist device.

FIG. 26 is a cross-sectional view of a dual function infusion/expansion pump 2600, having basically the combined function of the dual-spiral infusion pump 1555 of FIGS. 23 and 24, and the expansion pump 2500 of FIG. 25, for use as a breathing assist device, including its use as a CPAP device, a DPAP device, a breathing apparatus for diving.

In operation, during the inhalation stage 502 of the respiratory cycle of FIG. 5, the pump 2600 intakes air, oxygen, or another breathing gas 2340 through the port 2310 and compresses the gas 2340 for exhaust through the port 2323, as explained earlier. During the inhalation stage 502, the exhaust ports 2350, 2351, 2352, 2353, 2354, 2355 are closed to prevent the escape of the gas and to ensure increase pressure.

During the expiration stage 505, the exhaled carbon dioxide is pulled into the pump 2600 through the port 2323, and expanded to exhaust through the exhaust ports 2350, 2351, 2352, 2353, 2354, 2355, with the port 2310 being closed, to ensure that the carbon dioxide is not breathed in by the user.

Figure 27:
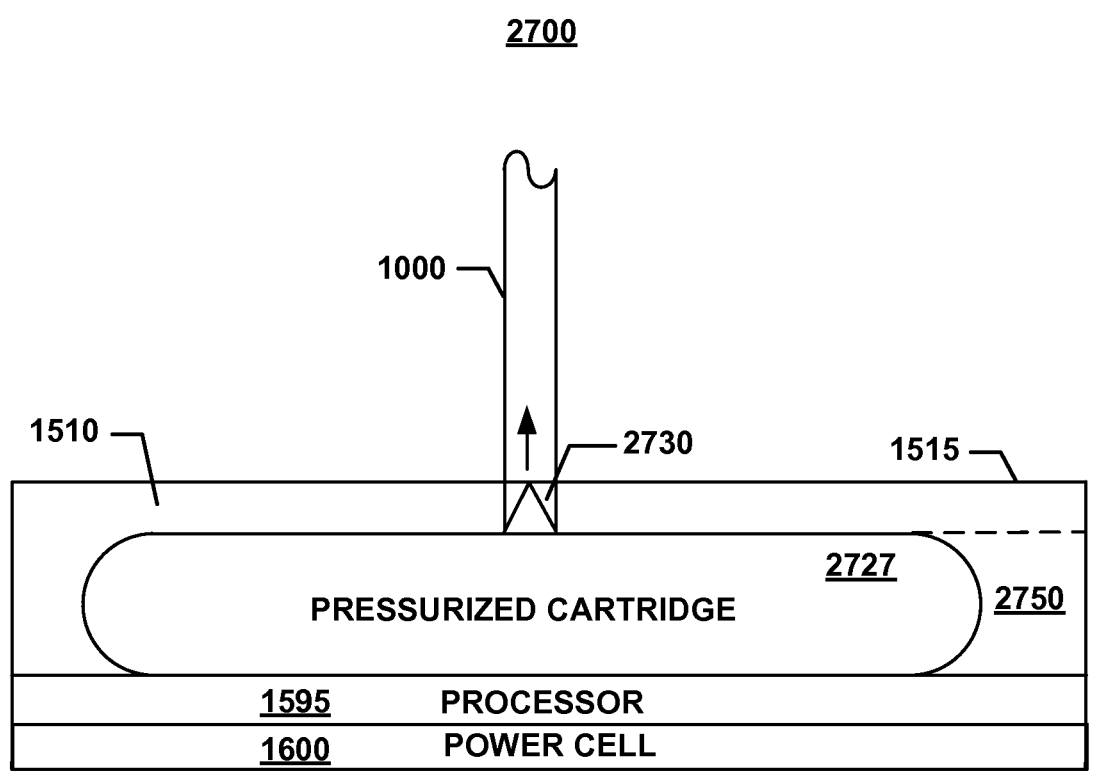
FIG. 27 is a block diagram of a DPAP device according to another embodiment of the present invention, shown using a pressurized cartridge as a stimulation source.

FIG. 27 represents a DPAP device 2700 according to another embodiment of the present invention, shown using a pressurized cartridge 2727 as a stimulation source. In this embodiment, the DPAP device 2700 uses the pressurized cartridge as its stimulation source, thus simplifying its operation and reducing its cost.

The DPAP device 2700 uses the processor 1595 to regulate the opening and closing of an outlet valve 2730, to deliver the stimulation, as described herein, via the nasal tube 1000. The pressurized cartridge 2727 can be filled with either air or another appropriate breathing gas, under pressure.

Since the use of the pressurized cartridge 2727 is limited during sleep, the size of the pressurized cartridge 2727 can be miniaturized. The pressurized cartridge 2727 can be replaced, as needed, by sliding it in and out of the body 1510 through an opening 2750.

While particular embodiments of the present invention have been disclosed, it is to be understood that various different modifications are possible and are contemplated within the scope of the specification, drawings, abstract and appended claims.

What is claimed is:

1. A portable, rechargeable, discontinuous positive airway pressure (DPAP) device for use by an individual as a breathing assist device, the DPAP device comprising:
   a sensor for tracking an exhalation phase of a respiration cycle of the individual relative to a stimulation period by providing an output reflective of any one or more of flow data and pressure data;
   a controller responsive to the sensor output for determining the entry of the exhalation phase into the stimulation period;
   a stimulation source responsive to a determination that the exhalation phase has entered the stimulation period near the end of the exhalation phase, for delivering a discontinuous stimulation, via a tube, only during the stimulation period sufficiently to induce a premature inhalation phase;
   the controller regulating the delivery of the discontinuous stimulation by the stimulation source;
   a rechargeable power cell for powering any one or more of the sensor, the stimulation source, and the controller; and
   wherein the rechargeable power cell includes a Seebeck element that is placed in contact with the individual's body for thermoelectrically converting the individual's body heat into an electrical current that recharges the power cell.

2. The DPAP device of claim 1, wherien the rechargeable power cell further includes any one or more of:
   a solar charger;
   a piezoelectric vibration element;
   a heat sink; and
   an inductive element.

3. The DPAP device of claim 1, wherein the stimulation source includes a dual-scroll infusion pump.

4. The DPAP device of claim 3, wherien the dual-scroll infusion pump compresses an input fluid; and
   wherein the dual-scroll infusion pump includes an output port that is connected to a nasal tube for delivering the compressed input fluid, as the stimulation, to a nasal-cavity.

5. The DPAP device of claim 1, further comprising a dental appliance that is placed, at least in part, within the individual's mouth; and
   wherein the stimulation source includes an output port that is connected to an oral tube for delivering compressed input fluid, as the stimulation, via the dental appliance.

6. The DPAP device of claim 5, wherein the dental appliance includes:
   a compliant section that fits over the individual's teeth, and an internal extension; and
   at least one opening that enables the stimulation to be nozzled out of any one or more of the compliant section and the internal extension, directionally toward an intended target stimulation area.

7. The DPAP device of claim 6, wherein the compliant section includes a pliable section that forms a resting seat for the teeth.

8. The DPAP device of claim 7, wherein during regular breathing events, the pliable section is fluidly open;
   further comprising a valve that is normally closed in the absence of teeth grinding; and
   wherein a grinding motion closes the pliable section of the resting seat, and a backpressure is built within the dental appliance, causing the valve to open and to direct the stimulation toward the intended target stimulation area.

9. The DPAP device of claim 1, further comprising a wireless communication channel that enables a remote communication with an external processor.

10. The DPAP device 1, wherein the stimulation device includes a continuous positive air pressure device.

11. The DPAP device 1, wherein the stimulation period precedes a virtual natural expiration point, $T_4$.

12. A portable, rechargeable, discontinuous positive airway pressure (DPAP) device for use by an individual as a breathing assist device, the DPAP device comprising:
   a sensor for tracking an exhalation phase of a respiration cycle of the individual relative to a stimulation period by providing an output reflective of any one or more of flow data and pressure data;
   a controller responsive to the sensor output for determining the entry of the exhalation phase into the stimulation period;
   a stimulation source responsive to a determination that the exhalation phase has entered the stimulation period near the end of the exhalation phase, for delivering a discontinuous stimulation, via a tube, only during the stimulation period sufficiently to induce a premature inhalation phase;
   the controller regulating the delivery of the discontinuous stimulation by the stimulation source; and
   wherein the stimulation source includes a portable pressurized cartridge.

13. The DPAP device of claim 1, wherein the discontinuous stimulation can be any one or more of: gradual or stepped.

14. The DPAP device of claim 1, wherein the tube includes a nasal cannula.

* * * * *